(12) United States Patent
Lubenau

(10) Patent No.: US 10,980,868 B2
(45) Date of Patent: Apr. 20, 2021

(54) VEGFR-2 TARGETING IMMUNOTHERAPY APPROACH

(71) Applicant: VAXIMM AG, Basel (CH)

(72) Inventor: Heinz Lubenau, Neustadt an der Weinstrasse (DE)

(73) Assignee: VAXIMM AG, Basel (CH)

( * ) Notice: Subject to any disclaimer, the term of this patent is extended or adjusted under 35 U.S.C. 154(b) by 1 day.

(21) Appl. No.: 16/486,425

(22) PCT Filed: Feb. 16, 2018

(86) PCT No.: PCT/EP2018/053918
§ 371 (c)(1),
(2) Date: Aug. 15, 2019

(87) PCT Pub. No.: WO2018/149982
PCT Pub. Date: Aug. 23, 2018

(65) Prior Publication Data
US 2020/0038496 A1 Feb. 6, 2020

(30) Foreign Application Priority Data
Feb. 17, 2017 (EP) ..................................... 17156718

(51) Int. Cl.
*A61K 39/00* (2006.01)
*A61P 35/00* (2006.01)

(52) U.S. Cl.
CPC .. *A61K 39/001109* (2018.08); *A61K 39/0011* (2013.01); *A61P 35/00* (2018.01); *A61K 2039/522* (2013.01); *A61K 2039/523* (2013.01); *A61K 2039/542* (2013.01)

(58) Field of Classification Search
None
See application file for complete search history.

(56) References Cited

U.S. PATENT DOCUMENTS 9,415,098 B2 * 8/2016 Lubenau ................. C07K 14/71
10,293,037 B2 * 5/2019 Lubenau ............ A61K 39/0011
10,441,645 B2 * 10/2019 Springer .................. C12N 1/20

FOREIGN PATENT DOCUMENTS

WO WO 2015/090584 A1 * 6/2015
WO WO2015142875 A1 9/2015
WO WO2016202459 A1 12/2016
WO WO2018011289 A1 1/2018

OTHER PUBLICATIONS

Zhao et al. Acta Med. Univ. Sci. Technol. Huszhong. 35: 490-491, 2006.*
Chen, Y. et al., "An Orally Administered DNA Vaccine Targeting Vascular Endothelial Growth Factor Receptor-3 Inhibits Lung Carcinoma Growth", Tumor Biol. 37(2): 2395-2404 (2015).
Su, J. et al., "Further Evidence for Expression and Function of the VEGF-C/VEGFR-3 Axis in Cancer Cells", Cancer Cell 13(6): 557-560 (Jun. 2008).
Schmitz-Winnenthal, F. et al., "Anti-angiogenic Activity of VXM01, an Oral T-cell Vaccine Against VEGF Receptor 2, in Patients with Advanced Pancreatic Cancer: A Randomized, Placebo-controlled, Phase 1 Trial", Oncoimmunology 4(4): e1001217 (Apr. 2015).
Kessler, T. et al., "Glioma Cell VEGFR-2 Confers Resistance to Chemotherapeutic and Antiangiogenic Treatments in PTEN-deficient Glioblastoma", Oncotarget, 6(31): 1050-31068 (2015).
Notification of Transmittal of International Search Report and the Written Opinion of the International Searching Authority, or the Declaration, for International App. No. PCT/EP2018/053918, dated Jun. 18, 2018 (22 pages).

* cited by examiner

*Primary Examiner* — Sarvamangala Devi
(74) *Attorney, Agent, or Firm* — McNeill Baur PLLC

(57) ABSTRACT

The present invention relates to an attenuated strain of *Salmonella* comprising at least one copy of a DNA molecule comprising an expression cassette encoding a VEGF receptor protein for use in cancer immunotherapy, wherein the cancer is characterized by VEGF receptor protein expressing cancer cells. The present invention further relates to an attenuated strain of *Salmonella* comprising at least one copy of a DNA molecule comprising an expression cassette encoding a VEGF receptor protein for use in cancer immunotherapy, wherein the cancer is characterized by VEGF receptor protein expressing cancer cells, and wherein the cancer is selected from the group consisting of glioblastoma, carcinoid cancer, kidney cancer, particularly renal cell carcinoma, thyroid cancer, lung cancer, particularly Non-Small Cell Lung Cancer (NSCLC), breast cancer, ovarian cancer, prostate cancer, gastrointestinal cancer, particularly colorectal cancer, more particularly colon cancer, and skin cancer, particularly melanoma. The present invention further relates to an attenuated strain of *Salmonella* comprising at least one copy of a DNA molecule comprising an expression cassette encoding a VEGF receptor protein for use in cancer immunotherapy in a patient comprising at least one VEGF receptor protein expressing cancer cell.

Figure 9:
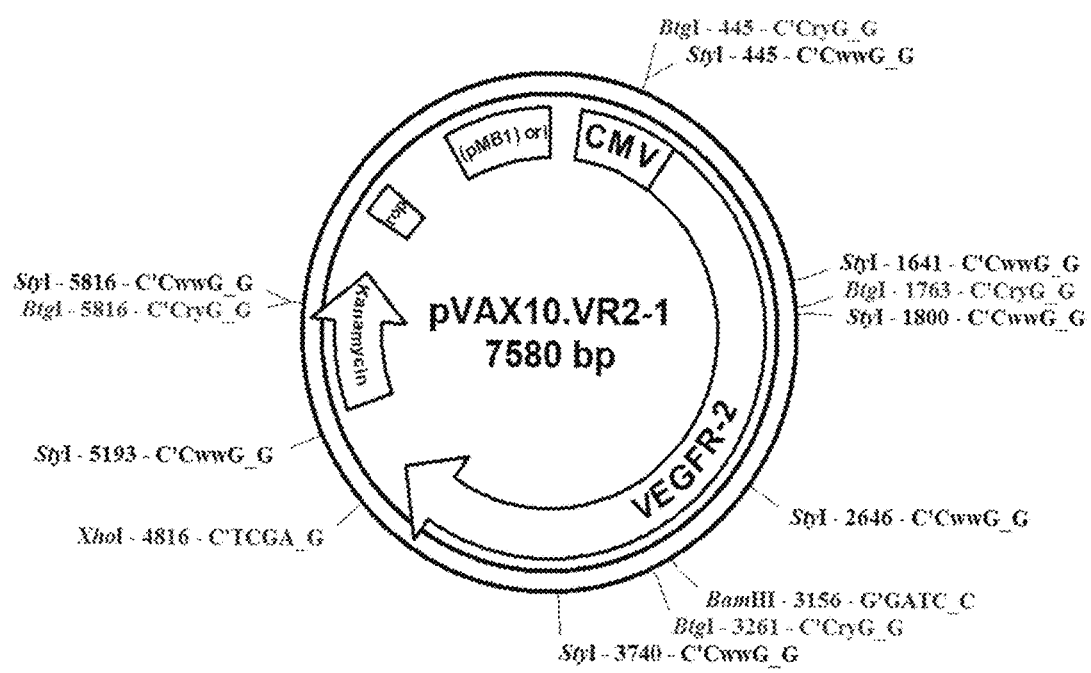

21 Claims, 14 Drawing Sheets
Specification includes a Sequence Listing.

Figure 1

```
          10         20         30         40         50         60
    MQSKVLLAVA LWLCVETRAA SVGLPSVSLD LPRLSIQKDI LTIKANTTLQ ITCRGQRDLD 70         80         90        100        110        120
    WLWPNNQSGS EQRVEVTECS DGLFCKTLTI PKVIGNDTGA YKCFYRETDL ASVIYVYVQD 130        140        150        160        170        180
    YRSPFIASVS DQHGVVYITE NKNKTVVIPC LGSISNLNVS LCARYPEKRF VPDGNRISWD 190        200        210        220        230        240
    SKKGFTIPSY MISYAGMVFC EAKINDESYQ SIMYIVVVG  YRIYDVVLSP SHGIELSVGE 250        260        270        280        290        300
    KLVLNCTART ELNVGIDFNW EYPSSKHQHK KLVNRDLKTQ SGSEMKKFLS TLTIDGVTRS 310        320        330        340        350        360
    DQGLYTCAAS SGLMTKKNST FVRVHEKPFV AFGSGMESLV EATVGERVRI PAKYLGYPPP 370        380        390        400        410        420
    EIKWYKNGIP LESNHTIKAG HVLTIMEVSE RDTGNYTVIL TNPISKEKQS HVVSLVVYVP 430        440        450        460        470        480
    PQIGEKSLIS PVDSYQYGTT QTLTCTVYAI PPPHHIHWYW QLEEECANEP SQAVSVTNPY 490        500        510        520        530        540
    PCEEWRSVED FQGGNKIEVN KNQFALIEGK NKTVSTLVIQ AANVSALYKC EAVNKVGRGE 550        560        570        580        590        600
    RVISFHVTRG PEITLQPDMQ PTEQESVSLW CTADRSTFEN LTWYKLGPQP LPIHVGELPT 610        620        630        640        650        660
    PVCKNLDTLW KLNATMFSNS TNDILIMELK NASLQDQGDY VCLAQDRKTK KRHCVVRQLT
```

Figure 1 (cont.)

```
            670        680        690        700        710        720
       VLERVAPTIT GNLENQTTSI GESIEVSCTA SGNPPPQIMW FKDNETLVED SGIVLKDGNR.

730        740        750        760        770        780
       NLTIRRVRKE DEGLYTCQAC SVLGCAKVEA FFIIEGAQEK TNLEIIILVG TAVIAMFFWL 790        800        810        820        830        840
       LLVIILRTVK RANGGELKTG YLSIVMDPDE LPLDEHCERL PYDASKWEFP RDRLKLGKPL 850        860        870        880        890        900
       GRGAFGQVIE ADAFGIDKTA TCRTVAVKML KEGATHSEHR ALMSELKILI HIGHHLNVVN 910        920        930        940        950        960
       LLGACTKPGG PLMVIVEFCK FGNLSTYLRS KRNEFVPYKT KGARFRQGKD YVGAIPVDLK 970        980        990       1000       1010       1020
       RRLDSITSSQ SSASSGFVEE KSLSDVEEEE APEDLYKDFL TLEHLICYSF QVAKGMEFLA 1030       1040       1050       1060       1070       1080
       SRKCIHRDLA ARNILLSEKN VVKICDFGLA RDIYKDPDYV RKGDARLPLK WMAPETIFDR 1090       1100       1110       1120       1130       1140
       VYTIQSDVWS FGVLLWEIFS LGASPYPGVK IDEEFCRRLK EGTRMRAPDY TTPEMYQTML 1150       1160       1170       1180       1190       1200
       DCWHGEPSQR PTFSELVEHL GNLLQANAQQ DGKDYIVLPI SETLSMEEDS GLSLPTSPVS 1210       1220       1230       1240       1250       1260
       CMEEEEVCDP KFHYDNTAGI SQYLQNSKRK SRPVSVKTFE DIPLEEPEVK VIPDDNQTDS 1270       1280       1290       1300       1310       1320
       GMVLASEELK TLEDRTKLSP SFGGMVPSKS RESVASEGSN QTSGYQSGYH SDDTDTTVYS
```

Figure 1 (cont.)

```
          1330       1340       1350
SEEAELLKLI EIGVQTGSTA QILQPDSGTT LSSPPV
```

Figure 2

```
TGGGCTTTTGCTGGCCTTTTGCTCACATGTTCTTGACTCTTCGCGATGTACGGGCCA
GATATACGCGTTGACATTGATTATTGACTAGTTATTAATAGTAATCAATTACGGGGTC
ATTAGTTCATAGCCCATATATGGAGTTCCGCGTTACATAACTTACGGTAAATGGCCC
GCCTGGCTGACCGCCCAACGACCCCCGCCCATTGACGTCAATAATGACGTATGTTC
CCATAGTAACGCCAATAGGGACTTTCCATTGACGTCAATGGGTGGACTATTTACGGT
AAACTGCCCACTTGGCAGTACATCAAGTGTATCATATGCCAAGTACGCCCCCTATTG
ACGTCAATGACGGTAAATGGCCCGCCTGGCATTATGCCCAGTACATGACCTTATGG
GACTTTCCTACTTGGCAGTACATCTACGTATTAGTCATCGCTATTACCATGGTGATG
CGGTTTTGGCAGTACATCAATGGGCGTGGATAGCGGTTTGACTCACGGGGATTTCC
AAGTCTCCACCCCATTGACGTCAATGGGAGTTTGTTTTGGCACCAAAATCAACGGG
ACTTTCCAAAATGTCGTAACAACTCCGCCCCATTGACGCAAATGGGCGGTAGGCGT
GTACGGTGGGAGGTCTATATAAGCAGAGCTCTCTGGCTAACTAGAGAACCCACTGC
TTACTGGCTTATCGAAATTAATACGACTCACTATAGGGAGACCCAAGCTGGCTAGCC
TCGAGTCTAGAGGGCCCGTTTAAACCCGCTGATCAGCCTCGACTGTGCCTTCTAGT
TGCCAGCCATCTGTTGTTTGCCCCTCCCCGTGCCTTCCTTGACCCTGGAAGGTGC
CACTCCCACTGTCCTTTCCTAATAAAATGAGGAAATTGCATCGCATTGTCTGAGTAG
GTGTCATTCTATTCTGGGGGGTGGGGTGGGGCAGGACAGCAAGGGGGAGGATTG
GGAAGACAATAGCAGGCATGCTGGGGATGCGGTGGGCTCTATGGCTTCTACTGGG
CGGTTTTATGGACAGCAAGCGAACCGGAATTGCCAGCTGGGGCGCCCTCTGGTAA
GGTTGGGAAGCCCTGCAAAGTAAACTGGATGGCTTTCTCGCCGCCAAGGATCTGAT
GGCGCAGGGGATCAAGCTCTGATCAAGAGACAGGATGAGGATCGTTTCGCATGATT
GAACAAGATGGATTGCACGCAGGTTCTCCGGCCGCTTGGGTGGAGAGGCTATTCG
GCTATGACTGGGCACAACAGACAATCGGCTGCTCTGATGCCGCCGTGTTCCGGCT
GTCAGCGCAGGGGCGCCCGGTTCTTTTTGTCAAGACCGACCTGTCCGGTGCCCTG
AATGAACTGCAAGACGAGGCAGCGCGGCTATCGTGGCTGGCCACGACGGGCGTTC
CTTGCGCAGCTGTGCTCGACGTTGTCACTGAAGCGGGAAGGGACTGGCTGCTATT
GGGCGAAGTGCCGGGGCAGGATCTCCTGTCATCTCACCTTGCTCCTGCCGAGAAA
GTATCCATCATGGCTGATGCAATGCGGCGGCTGCATACGCTTGATCCGGCTACCTG
CCCATTCGACCACCAAGCGAAACATCGCATCGAGCGAGCACGTACTCGGATGGAA
GCCGGTCTTGTCGATCAGGATGATCTGGACGAAGAGCATCAGGGGCTCGCGCCAG
CCGAACTGTTCGCCAGGCTCAAGGCGAGCATGCCCGACGGCGAGGATCTCGTCGT
GACCCATGGCGATGCCTGCTTGCCGAATATCATGGTGGAAAATGGCCGCTTTTCTG
GATTCATCGACTGTGGCCGGCTGGGTGTGGCGGACCGCTATCAGGACATAGCGTT
GGCTACCCGTGATATTGCTGAAGAGCTTGGCGGCGAATGGGCTGACCGCTTCCTC
GTGCTTTACGGTATCGCCGCTCCCGATTCGCAGCGCATCGCCTTCTATCGCCTTCT
TGACGAGTTCTTCTGAATTATTAACGCTTACAATTTCCTGATGCGGTATTTTCTCCTT
ACGCATCTGTGCGGTATTTCACACCGCATACAGGTGGCACTTTTCGGGGAAATGTG
CGCGGAACCCCTATTTGTTTATTTTTCTAAATACATTCAAATATGTATCCGCTCATGA
GACAATAACCCTGATAAATGCTTCAATAATAGCACGTGCTAAAACTTCATTTTTAATT
TAAAAGGATCTAGGTGAAGATCCTTTTTGATAATCTCATGACCAAAATCCCTTAACGT
GAGTTTTCGTTCCACTGAGCGTCAGACCCCATCAGTGACCAAACAGGAAAAACC
GCCCTTAACATGGCCCGCTTTATCAGAAGCCAGACATTAACGCTTCTGGAGAAACT
CAACGAGCTGGACGCGGATGAACAGGCAGACATCTGTGAATCGCTTCACGACCAC
```

Figure 2 (cont.)

```
GCTGATGAGCTTTACCGCAGCTGCCTCGCGCGTTTCGGTGATGACGGTGAAAACCT
CTGACACATGCAGCTCCCGGAGACGGTCACAGCTTGTCTGTAAGCGGATGCCGGG
AGCAGACAAGCCCGTCAGGGCGCGTCAGCGGGTGTTGGCGGGTGTCGGGGCGCA
GCCATGACCCAGTCACGTAGCGATAGCGGAGTGTATACTGGCTTAACTATGCGGCA
TCAGAGCAGATTGTACTGAGAGTGCACCATATGCGGTGTGAAATACCGCACAGATG
CGTAAGGAGAAAATACCGCATCAGGCGCTCTTCCGCTTCCTCGCTCACTGACTCGC
TGCGCTCGGTCGTTCGGCTGCGGCGAGCGGTATCAGCTCACTCAAAGGCGGTAAT
ACGGTTATCCACAGAATCAGGGGATAACGCAGGAAAGAACATGTGAGCAAAAGGCC
AGCAAAAGGCCAGGAACCGTAAAAAGGCCGCGTTGCTGGCGTTTTTCCATAGGCTC
CGCCCCCTGACGAGCATCACAAAAATCGACGCTCAAGTCAGAGGTGGCGAAACC
CGACAGGACTATAAAGATACCAGGCGTTTCCCCCTGGAAGCTCCCTCGTGCGCTCT
CCTGTTCCGACCCTGCCGCTTACCGGATACCTGTCCGCCTTTCTCCCTTCGGGAAG
CGTGGCGCTTTCTCATAGCTCACGCTGTAGGTATCTCAGTTCGGTGTAGGTCGTTC
GCTCCAAGCTGGGCTGTGTGCACGAACCCCCGTTCAGCCCGACCGCTGCGCCTT
ATCCGGTAACTATCGTCTTGAGTCCAACCCGGTAAGACACGACTTATCGCCACTGG
CAGCAGCCACTGGTAACAGGATTAGCAGAGCGAGGTATGTAGGCGGTGCTACAGA
GTTCTTGAAGTGGTGGCCTAACTACGGCTACACTAGAAGGACAGTATTTGGTATCTG
CGCTCTGCTGAAGCCAGTTACCTTCGGAAAAAGAGTTGGTAGCTCTTGATCCGGCA
AACAAACCACCGCTGGTAGCGGTGGTTTTTTTGTTTGCAAGCAGCAGATTACGCGC
AGAAAAAAAGGATCTCAAGAAGATCCTTTGATC
```

Figure 3

```
         10         20         30         40         50         60
MGSDVRDLNA LLPAVPSLGG GGGCALPVSG AAQWAPVLDF APPGASAYGS LGGPAPPPAP 70         80         90        100        110        120
PPPPPPPPHS FIKQEPSWGG AEPHEEQCLS AFTVHFSGQF TGTAGACRYG PFGPPPPSQA 130        140        150        160        170        180
SSGQARMFPN APYLPSCLES QPAIRNQGYS TVTFDGTPSY GHTPSHHAAQ FPNHSFKHED 190        200        210        220        230        240
PMGQQGSLGE QQYSVPPPVY GCHTPTDSCT GSQALLLRTP YSSDNLYQMT SQLECMTWNQ 250        260        270        280        290        300
MNLGATLKGV AAGSSSSVKW TEGQSNHSTG YESDNHTTPI LCGAQYRIHT HGVFRGIQDV 310        320        330        340        350        360
RRVPGVAPTL VRSASETSEK RPFMCAYPGC NKRYFKLSHL QMHSRKHTGE KPYQCDFKDC

370
ERRFSRSDQL K
```

Figure 4

MALPTARPLLGSCGTPALGSLLFLLFSLGWVQPSRTLAGETGQEAAPLDGVLANPPNISSLS
PRQLLGFPCAEVSGLSTERVRELAVALAQKNVKLSTEQLRCLAHRLSEPPEDLDALPLDLLL
FLNPDAFSGPQACTRFFSRITKANVDLLPRGAPERQRLLPAALACWGVRGSLLSEADVRAL
GGLACDLPGRFVAESAEVLLPRLVSCPGPLDQDQQEAARAALQGGGPPYGPPSTWSVST
MDALRGLLPVLGQPIIRSIPQGIVAAWRQRSSRDPSWRQPERTILRPRFRREVEKTACPSGK
KAREIDESLIFYKKWELEACVDAALLATQMDRVNAIPFTYEQLDVLKHKLDELYPQGYPESVI
QHLGYLFLKMSPEDIRKWNVTSLETLKALLEVNKGHEMSPQAPRRPLPQVATLIDRFVKGR
GQLDKDTLDTLTAFYPGYLCSLSPEELSSVPPSSIWAVRPQDLDTCDPRQLDVLYPKARLAF
QNMNGSEYFVKIQSFLGGAPTEDLKALSQQNVSMDLATFMKLRTDAVLPLTVAEVQKLLGP
HVEGLKAEERHRPVRDWILRQRQDDLDTLGLGLQGGIPNGYLVLDLSMQEALSGTPCLLGP
GPVLTVLALLLASTLA

Figure 5

MESPSAPPHRWCIPWQRLLLTASLLTFWNPPTTAKLTIESTPFNVAEGKEVLLLVHNLP
QHLFGYSWYKGERVDGNRQIIGYVIGTQQATPGPAYSGREIIYPNASLLIQNIIQNDTGFY
TLHVIKSDLVNEEATGQFRVYPELPKPSISSNNSKPVEDKDAVAFTCEPETQDATYLWW
VNNQSLPVSPRLQLSNGNRTLTLFNVTRNDTASYKCETQNPVSARRSDSVILNVLYGPD
APTISPLNTSYRSGENLNLSCHAASNPPAQYSWFVNGTFQQSTQELFIPNITVNNSGSY
TCQAHNSDTGLNRTTVTTITVYAEPPKPFITSNNSNPVEDEDAVALTCEPEIQNTTYLW
WVNNQSLPVSPRLQLSNDNRTLTLLSVTRNDVGPYECGIQNKLSVDHSDPVILNVLYGP
DDPTISPSYTYYRPGVNLSLSCHAASNPPAQYSWLIDGNIQQHTQELFISNITEKNSGLY
TCQANNSASGHSRTTVKTITVSAELPKPSISSNNSKPVEDKDAVAFTCEPEAQNTTYLW
WVNGQSLPVSPRLQLSNGNRTLTLFNVTRNDARAYVCGIQNSVSANRSDPVTLDVLYG
PDTPIISPPDSSYLSGANLNLSCHSASNPSPQYSWRINGIPQQHTQVLFIAKITPNNNGTY
ACFVSNLATGRNNSIVKSITVSASGTSPGLSAGATVGIMIGVLVGVALI

Figure 6

MESRGRRCPEMISVLGPISGHVLKAVFSRGDTPVLPHETRLLQTGIHVRVSQPSLILVSQ
YTPDSTPCHRGDNQLQVQHTYFTGSEVENVSVNVHNPTGRSICPSQEPMSIYVYALPL
KMLNIPSINVHHYPSAAERKHRHLPVADAVIHASGKQMWQARLTVSGLAWTRQQNQW
KEPDVYYTSAFVFPTKDVALRHVVCAHELVCSMENTRATKMQVIGDQYVKVYLESFCE
DVPSGKLFMHVTLGSDVEEDLTMTRNPQPFMRPHERNGFTVLCPKNMIIKPGKISHIML
DVAFTSHEHFGLLCPKSIPGLSISGNLLMNGQQIFLEVQAIRETVELRQYDPVAALFFFDI
DLLLQRGPQYSEHPTFTSQYRIQGKLEYRHTWDRHDEGAAQGDDDVWTSGSDSDEEL
VTTERKTPRVTGGGAMAGASTSAGRKRKSASSATACTAGVMTRGRLKAESTVAPEED
TDEDSDNEIHNPAVFTWPPWQAGILARNLVPMVATVQGQNLKYQEFFWDANDIYRIFA
ELEGVWQPAAQPKRRRHRQDALPGPCIASTPKKHRG

Figure 7

MESRGRRCPEMISVLGPISGHVLKAVFSRGDTPVLPHETRLLQTGIHVRVSQPSLILVSQ
YTPDSTPCHRGDNQLQVQHTYFTGSEVENVSVNVHNPTGRSICPSQEPMSIYVYALPL
KMLNIPSINVHHYPSAAERKHRHLPVADAVIHASGKQMWQARLTVSGLAWTRQQNQW
KEPDVYYTSAFVFPTKDVALRHVVCAHELVCSMENTRATKMQVIGDQYVKVYLESFCE
DVPSGKLFMHVTLGSDVEEDLTMTRNPQPFMRPHERNGFTVLCPKNMIIKPGKISHIML
DVAFTSHEHFGLLCPKSIPGLSISGNLLMNGQQIFLEVQAIRETVELRQYDPVAALFFFDI
DLLLQRGPQYSEHPTFTSQYRIQGKLEYRHTWDRHDEGAAQGDDDVWTSGSDSDEEL
VTTERKTPRVTGGGAMAGASTSAGRNRKSASSATACTAGVMTRGRLKAESTVAPEED
TDEDSDNEIHNPAVFTWPPWQAGILARNLVPMVATVQGQNLKYQEFFWDANDIYRIFA
ELEGVWQPAAQPKRRRHRQDALPGPCIASTPKKHRG

Figure 8

MESRGRRCPEMISVLGPISGHVLKAVFSRGDTPVLPHETRLLQTGIHVRVSQPSLILVSQ
YTPDSTPCHRGDNQLQVQHTYFTGSEVENVSVNVHNPTGRSICPSQEPMSIYVYALPL
KMLNIPSINVHHYPSAAERKHRHLPVADAVIHASGKQMWQARLTVSGLAWTRQQNQW
KEPDVYYTSAFVFPTKDVALRHVVCAHELVCSMENTRATKMQVIGDQYVKVYLESFCE
DVPSGKLFMHVTLGSDVEEDLTMTRNPQPFMRPHERNGFTVLCPKNMIIKPGKISHIML
DVAFTSHEHFGLLCPKSIPGLSISGNLLMNGQQIFLEVQAIRETVELRQYDPVAALFFFDI
DLLLQRGPQYSEHPTFTSQYRIQGKLEYRHTWDRHDEGAAQGDDDVWTSGSDSDEEL
VTTERKTPRVTGGGAMAGASTSAGRNRKSASSATACTAGVMTRGRLKAESTVAPEED
TDEDSDNEIHNPAVFTWPPWQAGILARNLVPMVATVQGQNLKYQEFFWDANDIYRIFA
ELEGVWQPAAQ

Figure 10A
Baseline
25,1 x 10,2 mm
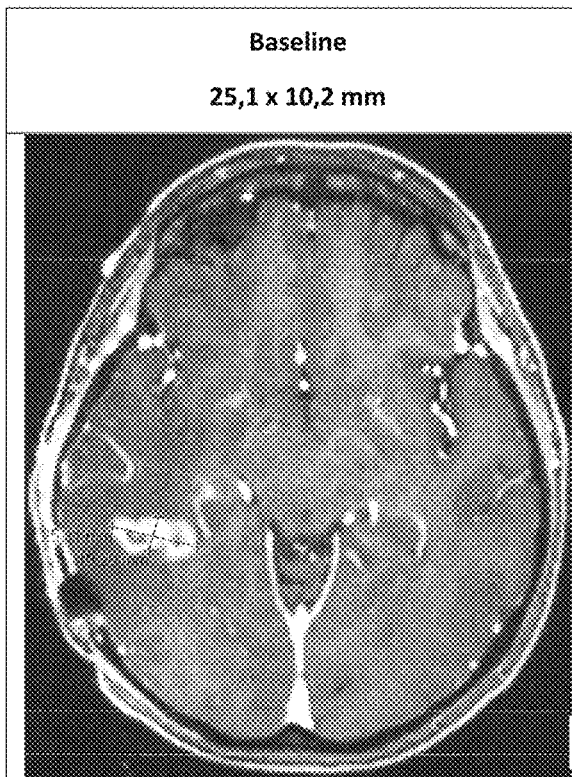
Figure 10B
Day 35 – Before Reoperation
24,6 x 12,3 mm
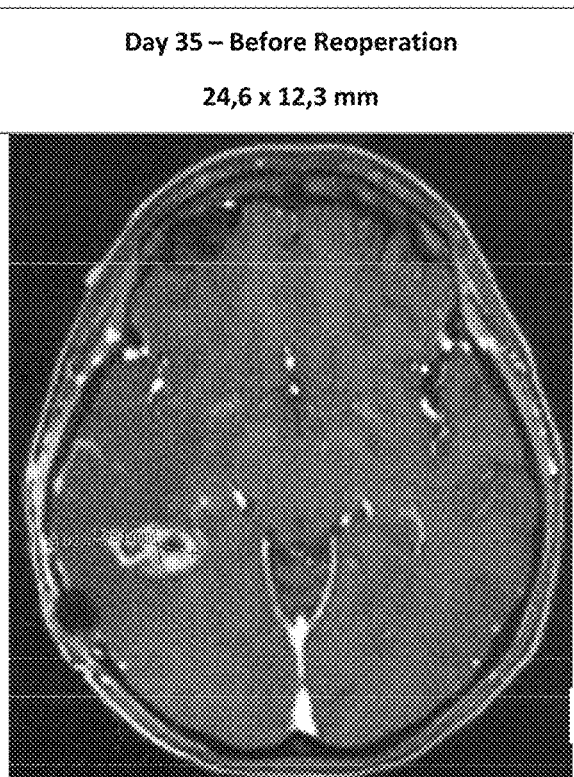
Week 12 – 7 Weeks after Reoperation
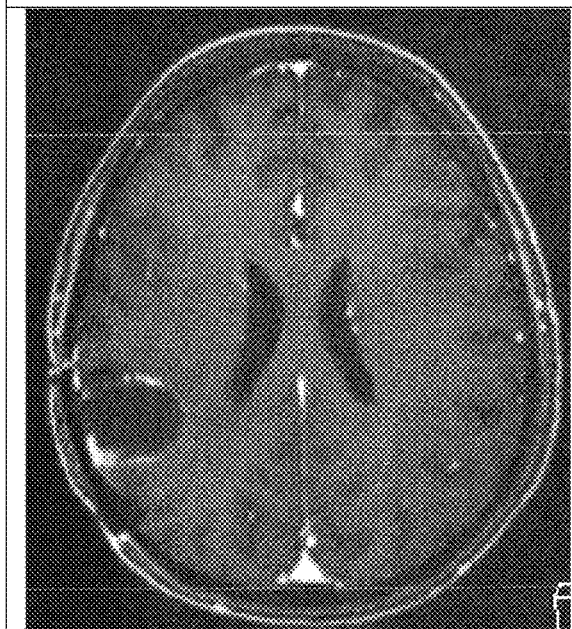
Figure 10C
Week 20 – 15 Weeks after Reoperation
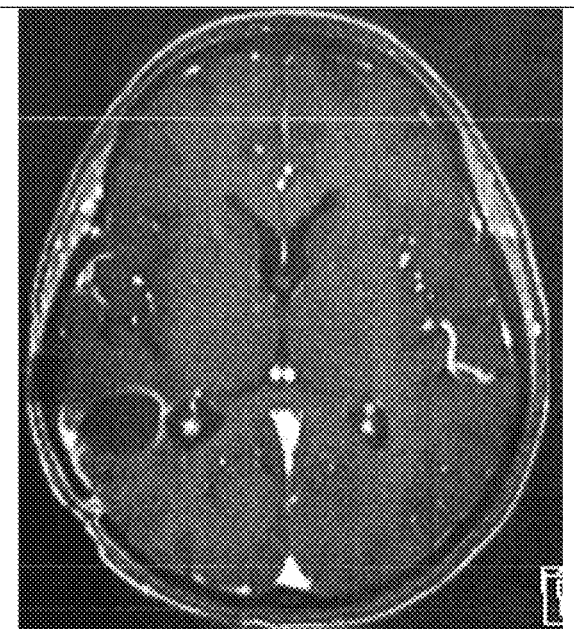
Figure 10D

SEQUENCE LISTING

```
<160> NUMBER OF SEQ ID NOS: 8

<210> SEQ ID NO 1
<211> LENGTH: 1356
<212> TYPE: PRT
<213> ORGANISM: Homo sapiens

<400> SEQUENCE: 1

Met Gln Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
            20                  25                  30

Arg Leu Ser Ile Gln Lys Asp Ile Leu Thr Ile Lys Ala Asn Thr Thr
```

```
                35                  40                  45
Leu Gln Ile Thr Cys Arg Gly Gln Arg Asp Leu Asp Trp Leu Trp Pro
 50                  55                  60
Asn Asn Gln Ser Gly Ser Glu Gln Arg Val Glu Val Thr Glu Cys Ser
 65                  70                  75                  80
Asp Gly Leu Phe Cys Lys Thr Leu Thr Ile Pro Lys Val Ile Gly Asn
                 85                  90                  95
Asp Thr Gly Ala Tyr Lys Cys Phe Tyr Arg Glu Thr Asp Leu Ala Ser
                100                 105                 110
Val Ile Tyr Val Tyr Val Gln Asp Tyr Arg Ser Pro Phe Ile Ala Ser
            115                 120                 125
Val Ser Asp Gln His Gly Val Val Tyr Ile Thr Glu Asn Lys Asn Lys
            130                 135                 140
Thr Val Val Ile Pro Cys Leu Gly Ser Ile Ser Asn Leu Asn Val Ser
145                 150                 155                 160
Leu Cys Ala Arg Tyr Pro Glu Lys Arg Phe Val Pro Asp Gly Asn Arg
                165                 170                 175
Ile Ser Trp Asp Ser Lys Lys Gly Phe Thr Ile Pro Ser Tyr Met Ile
                180                 185                 190
Ser Tyr Ala Gly Met Val Phe Cys Glu Ala Lys Ile Asn Asp Glu Ser
            195                 200                 205
Tyr Gln Ser Ile Met Tyr Ile Val Val Val Gly Tyr Arg Ile Tyr
            210                 215                 220
Asp Val Val Leu Ser Pro Ser His Gly Ile Glu Leu Ser Val Gly Glu
225                 230                 235                 240
Lys Leu Val Leu Asn Cys Thr Ala Arg Thr Glu Leu Asn Val Gly Ile
                245                 250                 255
Asp Phe Asn Trp Glu Tyr Pro Ser Ser Lys His Gln His Lys Lys Leu
                260                 265                 270
Val Asn Arg Asp Leu Lys Thr Gln Ser Gly Ser Glu Met Lys Lys Phe
            275                 280                 285
Leu Ser Thr Leu Thr Ile Asp Gly Val Thr Arg Ser Asp Gln Gly Leu
            290                 295                 300
Tyr Thr Cys Ala Ala Ser Ser Gly Leu Met Thr Lys Lys Asn Ser Thr
305                 310                 315                 320
Phe Val Arg Val His Glu Lys Pro Phe Val Ala Phe Gly Ser Gly Met
                325                 330                 335
Glu Ser Leu Val Glu Ala Thr Val Gly Glu Arg Val Arg Ile Pro Ala
            340                 345                 350
Lys Tyr Leu Gly Tyr Pro Pro Pro Glu Ile Lys Trp Tyr Lys Asn Gly
            355                 360                 365
Ile Pro Leu Glu Ser Asn His Thr Ile Lys Ala Gly His Val Leu Thr
            370                 375                 380
Ile Met Glu Val Ser Glu Arg Asp Thr Gly Asn Tyr Thr Val Ile Leu
385                 390                 395                 400
Thr Asn Pro Ile Ser Lys Glu Lys Gln Ser His Val Val Ser Leu Val
                405                 410                 415
Val Tyr Val Pro Pro Gln Ile Gly Glu Lys Ser Leu Ile Ser Pro Val
            420                 425                 430
Asp Ser Tyr Gln Tyr Gly Thr Thr Gln Thr Leu Thr Cys Thr Val Tyr
            435                 440                 445
Ala Ile Pro Pro Pro His His Ile His Trp Tyr Trp Gln Leu Glu Glu
            450                 455                 460
```

-continued

```
Glu Cys Ala Asn Glu Pro Ser Gln Ala Val Ser Val Thr Asn Pro Tyr
465                 470                 475                 480

Pro Cys Glu Glu Trp Arg Ser Val Glu Asp Phe Gln Gly Gly Asn Lys
                485                 490                 495

Ile Glu Val Asn Lys Asn Gln Phe Ala Leu Ile Glu Gly Lys Asn Lys
                500                 505                 510

Thr Val Ser Thr Leu Val Ile Gln Ala Ala Asn Val Ser Ala Leu Tyr
            515                 520                 525

Lys Cys Glu Ala Val Asn Lys Val Gly Arg Gly Glu Arg Val Ile Ser
            530                 535                 540

Phe His Val Thr Arg Gly Pro Glu Ile Thr Leu Gln Pro Asp Met Gln
545                 550                 555                 560

Pro Thr Glu Gln Glu Ser Val Ser Leu Trp Cys Thr Ala Asp Arg Ser
                565                 570                 575

Thr Phe Glu Asn Leu Thr Trp Tyr Lys Leu Gly Pro Gln Pro Leu Pro
                580                 585                 590

Ile His Val Gly Glu Leu Pro Thr Pro Val Cys Lys Asn Leu Asp Thr
            595                 600                 605

Leu Trp Lys Leu Asn Ala Thr Met Phe Ser Asn Ser Thr Asn Asp Ile
            610                 615                 620

Leu Ile Met Glu Leu Lys Asn Ala Ser Leu Gln Asp Gln Gly Asp Tyr
625                 630                 635                 640

Val Cys Leu Ala Gln Asp Arg Lys Thr Lys Arg His Cys Val Val
                645                 650                 655

Arg Gln Leu Thr Val Leu Glu Arg Val Ala Pro Thr Ile Thr Gly Asn
                660                 665                 670

Leu Glu Asn Gln Thr Thr Ser Ile Gly Glu Ser Ile Glu Val Ser Cys
            675                 680                 685

Thr Ala Ser Gly Asn Pro Pro Pro Gln Ile Met Trp Phe Lys Asp Asn
690                 695                 700

Glu Thr Leu Val Glu Asp Ser Gly Ile Val Leu Lys Asp Gly Asn Arg
705                 710                 715                 720

Asn Leu Thr Ile Arg Arg Val Arg Lys Glu Asp Glu Gly Leu Tyr Thr
                725                 730                 735

Cys Gln Ala Cys Ser Val Leu Gly Cys Ala Lys Val Glu Ala Phe Phe
            740                 745                 750

Ile Ile Glu Gly Ala Gln Glu Lys Thr Asn Leu Glu Ile Ile Ile Leu
            755                 760                 765

Val Gly Thr Ala Val Ile Ala Met Phe Phe Trp Leu Leu Leu Val Ile
            770                 775                 780

Ile Leu Arg Thr Val Lys Arg Ala Asn Gly Gly Glu Leu Lys Thr Gly
785                 790                 795                 800

Tyr Leu Ser Ile Val Met Asp Pro Asp Glu Leu Pro Leu Asp Glu His
                805                 810                 815

Cys Glu Arg Leu Pro Tyr Asp Ala Ser Lys Trp Glu Phe Pro Arg Asp
                820                 825                 830

Arg Leu Lys Leu Gly Lys Pro Leu Gly Arg Gly Ala Phe Gly Gln Val
                835                 840                 845

Ile Glu Ala Asp Ala Phe Gly Ile Asp Lys Thr Ala Thr Cys Arg Thr
            850                 855                 860

Val Ala Val Lys Met Leu Lys Glu Gly Ala Thr His Ser Glu His Arg
865                 870                 875                 880
```

-continued

Ala Leu Met Ser Glu Leu Lys Ile Leu Ile His Ile Gly His His Leu
              885                 890                 895

Asn Val Val Asn Leu Leu Gly Ala Cys Thr Lys Pro Gly Gly Pro Leu
              900                 905                 910

Met Val Ile Val Glu Phe Cys Lys Phe Gly Asn Leu Ser Thr Tyr Leu
              915                 920                 925

Arg Ser Lys Arg Asn Glu Phe Val Pro Tyr Lys Thr Lys Gly Ala Arg
              930                 935                 940

Phe Arg Gln Gly Lys Asp Tyr Val Gly Ala Ile Pro Val Asp Leu Lys
945                 950                 955                 960

Arg Arg Leu Asp Ser Ile Thr Ser Ser Gln Ser Ser Ala Ser Ser Gly
              965                 970                 975

Phe Val Glu Glu Lys Ser Leu Ser Asp Val Glu Glu Glu Ala Pro
              980                 985                 990

Glu Asp Leu Tyr Lys Asp Phe Leu Thr Leu Glu His Leu Ile Cys Tyr
              995                 1000                1005

Ser Phe Gln Val Ala Lys Gly Met Glu Phe Leu Ala Ser Arg Lys Cys
       1010                1015                1020

Ile His Arg Asp Leu Ala Ala Arg Asn Ile Leu Leu Ser Glu Lys Asn
1025                1030                1035                1040

Val Val Lys Ile Cys Asp Phe Gly Leu Ala Arg Asp Ile Tyr Lys Asp
              1045                1050                1055

Pro Asp Tyr Val Arg Lys Gly Asp Ala Arg Leu Pro Leu Lys Trp Met
              1060                1065                1070

Ala Pro Glu Thr Ile Phe Asp Arg Val Tyr Thr Ile Gln Ser Asp Val
       1075                1080                1085

Trp Ser Phe Gly Val Leu Leu Trp Glu Ile Phe Ser Leu Gly Ala Ser
       1090                1095                1100

Pro Tyr Pro Gly Val Lys Ile Asp Glu Glu Phe Cys Arg Arg Leu Lys
1105                1110                1115                1120

Glu Gly Thr Arg Met Arg Ala Pro Asp Tyr Thr Thr Pro Glu Met Tyr
              1125                1130                1135

Gln Thr Met Leu Asp Cys Trp His Gly Glu Pro Ser Gln Arg Pro Thr
              1140                1145                1150

Phe Ser Glu Leu Val Glu His Leu Gly Asn Leu Leu Gln Ala Asn Ala
       1155                1160                1165

Gln Gln Asp Gly Lys Asp Tyr Ile Val Leu Pro Ile Ser Glu Thr Leu
       1170                1175                1180

Ser Met Glu Glu Asp Ser Gly Leu Ser Leu Pro Thr Ser Pro Val Ser
1185                1190                1195                1200

Cys Met Glu Glu Glu Val Cys Asp Pro Lys Phe His Tyr Asp Asn
              1205                1210                1215

Thr Ala Gly Ile Ser Gln Tyr Leu Gln Asn Ser Lys Arg Lys Ser Arg
       1220                1225                1230

Pro Val Ser Val Lys Thr Phe Glu Asp Ile Pro Leu Glu Glu Pro Glu
       1235                1240                1245

Val Lys Val Ile Pro Asp Asp Asn Gln Thr Asp Ser Gly Met Val Leu
1250                1255                1260

Ala Ser Glu Glu Leu Lys Thr Leu Glu Asp Arg Thr Lys Leu Ser Pro
1265                1270                1275                1280

Ser Phe Gly Gly Met Val Pro Ser Lys Ser Arg Glu Ser Val Ala Ser
              1285                1290                1295

Glu Gly Ser Asn Gln Thr Ser Gly Tyr Gln Ser Gly Tyr His Ser Asp

```
                        1300              1305              1310
Asp Thr Asp Thr Thr Val Tyr Ser Ser Glu Glu Ala Glu Leu Leu Lys
            1315              1320              1325

Leu Ile Glu Ile Gly Val Gln Thr Gly Ser Thr Ala Gln Ile Leu Gln
        1330              1335              1340

Pro Asp Ser Gly Thr Thr Leu Ser Ser Pro Pro Val
1345              1350              1355

<210> SEQ ID NO 2
<211> LENGTH: 3500
<212> TYPE: DNA
<213> ORGANISM: artificial sequence
<220> FEATURE:
<223> OTHER INFORMATION: expression plasmid

<400> SEQUENCE: 2
tgggcttttg ctggcctttt gctcacatgt tcttgactct tcgcgatgta cgggccagat      60
atacgcgttg acattgatta ttgactagtt attaatagta atcaattacg ggtcattag     120
ttcatagccc atatatggag ttccgcgtta cataacttac ggtaaatggc ccgcctggct    180
gaccgcccaa cgaccccgc ccattgacgt caataatgac gtatgttccc atagtaacgc    240
caatagggac tttccattga cgtcaatggg tggactattt acggtaaact gcccacttgg    300
cagtacatca agtgtatcat atgccaagta cgccccctat tgacgtcaat gacggtaaat    360
ggcccgcctg gcattatgcc cagtacatga ccttatggga ctttcctact ggcagtaca    420
tctacgtatt agtcatcgct attaccatgg tgatgcggtt ttggcagtac atcaatgggc    480
gtggatagcg gtttgactca cggggatttc caagtctcca ccccattgac gtcaatggga    540
gtttgttttg gcaccaaaat caacgggact ttccaaaatg tcgtaacaac tccgccccat    600
tgacgcaaat gggcggtagg cgtgtacggt gggaggtcta taagcaga gctctctggc     660
taactagaga acccactgct tactggctta tcgaaattaa tacgactcac tatagggaga    720
cccaagctgg ctagcctcga gtctagaggg cccgtttaaa cccgctgatc agcctcgact    780
gtgccttcta gttgccagcc atctgttgtt tgccccctccc ccgtgccttc cttgaccctg    840
gaaggtgcca ctcccactgt cctttcctaa taaaatgagg aaattgcatc gcattgtctg    900
agtaggtgtc attctattct ggggggtggg gtggggcagg acagcaaggg ggaggattgg    960
gaagacaata gcaggcatgc tggggatgcg gtgggctcta tggcttctac tgggcggttt   1020
tatggacagc aagcgaaccg gaattgccag ctggggcgcc ctctggtaag gttgggaagc   1080
cctgcaaagt aaactggatg gctttctcgc cgccaaggat ctgatggcgc aggggatcaa   1140
gctctgatca agagacagga tgaggatcgt ttcgcatgat tgaacaagat ggattgcacg   1200
caggttctcc ggccgcttgg gtggagaggc tattcggcta tgactgggca acagacaa    1260
tcggctgctc tgatgccgcc gtgttccggc tgtcagcgca ggggcgcccg gttcttttg    1320
tcaagaccga cctgtccggt gccctgaatg aactgcaaga cgaggcagcg cggctatcgt   1380
ggctggccac gacgggcgtt ccttgcgcag ctgtgctcga cgttgtcact gaagcgggaa   1440
gggactggct gctattgggc gaagtgccgg ggcaggatct cctgtcatct caccttgctc   1500
ctgccgagaa agtatccatc atggctgatg caatgcggcg gctgcatacg cttgatccgg   1560
ctacctgccc attcgaccac caagcgaaac atcgcatcga gcgagcacgt actcggatgg   1620
aagccggtct tgtcgatcag gatgatctgg acgaagagca tcaggggctc gcgccagccg   1680
aactgttcgc caggctcaag gcgagcatgc ccgacggcga ggatctcgtc gtgacccatg   1740
```

```
gcgatgcctg cttgccgaat atcatggtgg aaaatggccg ctttttctgga ttcatcgact    1800
gtggccggct gggtgtggcg gaccgctatc aggacatagc gttggctacc cgtgatattg    1860
ctgaagagct tggcggcgaa tgggctgacc gcttcctcgt gctttacggt atcgccgctc    1920
ccgattcgca gcgcatcgcc ttctatcgcc ttcttgacga gttcttctga attattaacg    1980
cttacaattt cctgatgcgg tattttctcc ttacgcatct gtgcggtatt tcacaccgca    2040
tacaggtggc acttttcggg gaaatgtgcg cggaaccccct attgtttat ttttctaaat    2100
acattcaaat atgtatccgc tcatgagaca ataaccctga taaatgcttc aataatagca    2160
cgtgctaaaa cttcattttt aatttaaaag gatctaggtg aagatccttt ttgataatct    2220
catgaccaaa atcccttaac gtgagttttc gttccactga gcgtcagacc cccatcagtg    2280
accaaacagg aaaaaaccgc ccttaacatg cccgcttta tcagaagcca gacattaacg    2340
cttctggaga aactcaacga gctggacgcg gatgaacagg cagacatctg tgaatcgctt    2400
cacgaccacg ctgatgagct ttaccgcagc tgcctcgcgc gtttcggtga tgacggtgaa    2460
aacctctgac acatgcagct cccggagacg gtcacagctt gtctgtaagc ggatgccggg    2520
agcagacaag cccgtcaggg cgcgtcaggg ggtgttggcg ggtgtcgggg cgcagccatg    2580
acccagtcac gtagcgatag cggagtgtat actggcttaa ctatgcggca tcagagcaga    2640
ttgtactgag agtgcaccat atgcggtgtg aaataccgca cagatgcgta aggagaaaat    2700
accgcatcag gcgctcttcc gcttcctcgc tcactgactc gctgcgctcg tcgttcggc    2760
tgcggcgagc ggtatcagct cactcaaagg cggtaatacg ttatccaca gaatcagggg    2820
ataacgcagg aaagaacatg tgagcaaaag gccagcaaaa ggccaggaac cgtaaaaagg    2880
ccgcgttgct ggcgtttttc cataggctcc gcccccctga cgagcatcac aaaaatcgac    2940
gctcaagtca gaggtggcga aacccgacag gactataaag ataccaggcg tttccccctg    3000
gaagctccct cgtgcgctct cctgttccga ccctgccgct taccggatac ctgtccgcct    3060
ttctcccttc gggaagcgtg cgctttctc atagctcacg ctgtaggtat ctcagttcgg    3120
tgtaggtcgt tcgctccaag ctgggctgtg tgcacgaacc ccccgttcag cccgaccgct    3180
gcgccttatc cggtaactat cgtcttgagt ccaacccgt aagacacgac ttatcgccac    3240
tggcagcagc cactggtaac aggattagca gagcgaggta tgtaggcggt gctacagagt    3300
tcttgaagtg gtggcctaac tacggctaca ctagaaggac agtatttggt atctgcgctc    3360
tgctgaagcc agttaccttc ggaaaaagag ttggtagctc ttgatccggc aaacaaacca    3420
ccgctggtag cggtggtttt tttgtttgca agcagcagat tacgcgcaga aaaaaggat    3480
ctcaagaaga tcctttgatc                                                3500
```

<210> SEQ ID NO 3
<211> LENGTH: 371
<212> TYPE: PRT
<213> ORGANISM: Homo sapiens

<400> SEQUENCE: 3

```
Met Gly Ser Asp Val Arg Asp Leu Asn Ala Leu Leu Pro Ala Val Pro
1               5                   10                  15

Ser Leu Gly Gly Gly Gly Gly Cys Ala Leu Pro Val Ser Gly Ala Ala
            20                  25                  30

Gln Trp Ala Pro Val Leu Asp Phe Ala Pro Pro Gly Ala Ser Ala Tyr
        35                  40                  45

Gly Ser Leu Gly Gly Pro Ala Pro Pro Pro Ala Pro Pro Pro Pro Pro
    50                  55                  60
```

```
Pro Pro Pro Pro His Ser Phe Ile Lys Gln Glu Pro Ser Trp Gly Gly
65                  70                  75                  80

Ala Glu Pro His Glu Glu Gln Cys Leu Ser Ala Phe Thr Val His Phe
                85                  90                  95

Ser Gly Gln Phe Thr Gly Thr Ala Gly Ala Cys Arg Tyr Gly Pro Phe
            100                 105                 110

Gly Pro Pro Pro Ser Gln Ala Ser Ser Gly Gln Ala Arg Met Phe
            115                 120                 125

Pro Asn Ala Pro Tyr Leu Pro Ser Cys Leu Glu Ser Gln Pro Ala Ile
130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
            180                 185                 190

Tyr Ser Val Pro Pro Val Tyr Gly Cys His Thr Pro Thr Asp Ser
            195                 200                 205

Cys Thr Gly Ser Gln Ala Leu Leu Leu Arg Thr Pro Tyr Ser Ser Asp
210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
                245                 250                 255

Ser Val Lys Trp Thr Glu Gly Gln Ser Asn His Ser Thr Gly Tyr Glu
            260                 265                 270

Ser Asp Asn His Thr Thr Pro Ile Leu Cys Gly Ala Gln Tyr Arg Ile
            275                 280                 285

His Thr His Gly Val Phe Arg Gly Ile Gln Asp Val Arg Arg Val Pro
290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
            340                 345                 350

Tyr Gln Cys Asp Phe Lys Asp Cys Glu Arg Arg Phe Ser Arg Ser Asp
            355                 360                 365

Gln Leu Lys
370

<210> SEQ ID NO 4
<211> LENGTH: 630
<212> TYPE: PRT
<213> ORGANISM: Homo sapiens

<400> SEQUENCE: 4

Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
                20                  25                  30

Pro Ser Arg Thr Leu Ala Gly Glu Thr Gly Gln Glu Ala Ala Pro Leu
            35                  40                  45

Asp Gly Val Leu Ala Asn Pro Pro Asn Ile Ser Ser Leu Ser Pro Arg
```

```
                50                  55                  60
Gln Leu Leu Gly Phe Pro Cys Ala Glu Val Ser Gly Leu Ser Thr Glu
 65                  70                  75                  80

Arg Val Arg Glu Leu Ala Val Ala Leu Ala Gln Lys Asn Val Lys Leu
                 85                  90                  95

Ser Thr Glu Gln Leu Arg Cys Leu Ala His Arg Leu Ser Glu Pro Pro
                100                 105                 110

Glu Asp Leu Asp Ala Leu Pro Leu Asp Leu Leu Phe Leu Asn Pro
                115                 120                 125

Asp Ala Phe Ser Gly Pro Gln Ala Cys Thr Arg Phe Phe Ser Arg Ile
    130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
                180                 185                 190

Pro Gly Arg Phe Val Ala Glu Ser Ala Glu Val Leu Leu Pro Arg Leu
                195                 200                 205

Val Ser Cys Pro Gly Pro Leu Asp Gln Asp Gln Gln Glu Ala Ala Arg
210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
                260                 265                 270

Gln Arg Ser Ser Arg Asp Pro Ser Trp Arg Gln Pro Glu Arg Thr Ile
                275                 280                 285

Leu Arg Pro Arg Phe Arg Arg Glu Val Glu Lys Thr Ala Cys Pro Ser
    290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
                340                 345                 350

Lys His Lys Leu Asp Glu Leu Tyr Pro Gln Gly Tyr Pro Glu Ser Val
                355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Ala Pro Arg Arg Pro Leu
                405                 410                 415

Pro Gln Val Ala Thr Leu Ile Asp Arg Phe Val Lys Gly Arg Gly Gln
                420                 425                 430

Leu Asp Lys Asp Thr Leu Asp Thr Leu Thr Ala Phe Tyr Pro Gly Tyr
    435                 440                 445

Leu Cys Ser Leu Ser Pro Glu Glu Leu Ser Ser Val Pro Pro Ser Ser
    450                 455                 460

Ile Trp Ala Val Arg Pro Gln Asp Leu Asp Thr Cys Asp Pro Arg Gln
465                 470                 475                 480
```

```
Leu Asp Val Leu Tyr Pro Lys Ala Arg Leu Ala Phe Gln Asn Met Asn
                485                 490                 495

Gly Ser Glu Tyr Phe Val Lys Ile Gln Ser Phe Leu Gly Gly Ala Pro
            500                 505                 510

Thr Glu Asp Leu Lys Ala Leu Ser Gln Gln Asn Val Ser Met Asp Leu
        515                 520                 525

Ala Thr Phe Met Lys Leu Arg Thr Asp Ala Val Leu Pro Leu Thr Val
    530                 535                 540

Ala Glu Val Gln Lys Leu Leu Gly Pro His Val Glu Gly Leu Lys Ala
545                 550                 555                 560

Glu Glu Arg His Arg Pro Val Arg Asp Trp Ile Leu Arg Gln Arg Gln
                565                 570                 575

Asp Asp Leu Asp Thr Leu Gly Leu Gly Leu Gln Gly Gly Ile Pro Asn
            580                 585                 590

Gly Tyr Leu Val Leu Asp Leu Ser Met Gln Glu Ala Leu Ser Gly Thr
        595                 600                 605

Pro Cys Leu Leu Gly Pro Gly Pro Val Leu Thr Val Leu Ala Leu Leu
    610                 615                 620

Leu Ala Ser Thr Leu Ala
625                 630

<210> SEQ ID NO 5
<211> LENGTH: 702
<212> TYPE: PRT
<213> ORGANISM: Homo sapiens

<400> SEQUENCE: 5

Met Glu Ser Pro Ser Ala Pro Pro His Arg Trp Cys Ile Pro Trp Gln
1               5                   10                  15

Arg Leu Leu Leu Thr Ala Ser Leu Leu Thr Phe Trp Asn Pro Pro Thr
                20                  25                  30

Thr Ala Lys Leu Thr Ile Glu Ser Thr Pro Phe Asn Val Ala Glu Gly
            35                  40                  45

Lys Glu Val Leu Leu Leu Val His Asn Leu Pro Gln His Leu Phe Gly
50                  55                  60

Tyr Ser Trp Tyr Lys Gly Glu Arg Val Asp Gly Asn Arg Gln Ile Ile
65                  70                  75                  80

Gly Tyr Val Ile Gly Thr Gln Gln Ala Thr Pro Gly Pro Ala Tyr Ser
                85                  90                  95

Gly Arg Glu Ile Ile Tyr Pro Asn Ala Ser Leu Leu Ile Gln Asn Ile
            100                 105                 110

Ile Gln Asn Asp Thr Gly Phe Tyr Thr Leu His Val Ile Lys Ser Asp
        115                 120                 125

Leu Val Asn Glu Glu Ala Thr Gly Gln Phe Arg Val Tyr Pro Glu Leu
    130                 135                 140

Pro Lys Pro Ser Ile Ser Ser Asn Asn Ser Lys Pro Val Glu Asp Lys
145                 150                 155                 160

Asp Ala Val Ala Phe Thr Cys Glu Pro Glu Thr Gln Asp Ala Thr Tyr
                165                 170                 175

Leu Trp Trp Val Asn Asn Gln Ser Leu Pro Val Ser Pro Arg Leu Gln
            180                 185                 190

Leu Ser Asn Gly Asn Arg Thr Leu Thr Leu Phe Asn Val Thr Arg Asn
        195                 200                 205

Asp Thr Ala Ser Tyr Lys Cys Glu Thr Gln Asn Pro Val Ser Ala Arg
```

```
              210                 215                 220
Arg Ser Asp Ser Val Ile Leu Asn Val Leu Tyr Gly Pro Asp Ala Pro
225                 230                 235                 240

Thr Ile Ser Pro Leu Asn Thr Ser Tyr Arg Ser Gly Glu Asn Leu Asn
                245                 250                 255

Leu Ser Cys His Ala Ala Ser Asn Pro Pro Ala Gln Tyr Ser Trp Phe
                260                 265                 270

Val Asn Gly Thr Phe Gln Gln Ser Thr Gln Glu Leu Phe Ile Pro Asn
            275                 280                 285

Ile Thr Val Asn Asn Ser Gly Ser Tyr Thr Cys Gln Ala His Asn Ser
        290                 295                 300

Asp Thr Gly Leu Asn Arg Thr Thr Val Thr Thr Ile Thr Val Tyr Ala
305                 310                 315                 320

Glu Pro Pro Lys Pro Phe Ile Thr Ser Asn Asn Ser Asn Pro Val Glu
                325                 330                 335

Asp Glu Asp Ala Val Ala Leu Thr Cys Glu Pro Glu Ile Gln Asn Thr
                340                 345                 350

Thr Tyr Leu Trp Trp Val Asn Asn Gln Ser Leu Pro Val Ser Pro Arg
            355                 360                 365

Leu Gln Leu Ser Asn Asp Asn Arg Thr Leu Thr Leu Leu Ser Val Thr
370                 375                 380

Arg Asn Asp Val Gly Pro Tyr Glu Cys Gly Ile Gln Asn Lys Leu Ser
385                 390                 395                 400

Val Asp His Ser Asp Pro Val Ile Leu Asn Val Leu Tyr Gly Pro Asp
                405                 410                 415

Asp Pro Thr Ile Ser Pro Ser Tyr Thr Tyr Tyr Arg Pro Gly Val Asn
                420                 425                 430

Leu Ser Leu Ser Cys His Ala Ala Ser Asn Pro Pro Ala Gln Tyr Ser
            435                 440                 445

Trp Leu Ile Asp Gly Asn Ile Gln Gln His Thr Gln Glu Leu Phe Ile
            450                 455                 460

Ser Asn Ile Thr Glu Lys Asn Ser Gly Leu Tyr Thr Cys Gln Ala Asn
465                 470                 475                 480

Asn Ser Ala Ser Gly His Ser Arg Thr Thr Val Lys Thr Ile Thr Val
                485                 490                 495

Ser Ala Glu Leu Pro Lys Pro Ser Ile Ser Ser Asn Asn Ser Lys Pro
            500                 505                 510

Val Glu Asp Lys Asp Ala Val Ala Phe Thr Cys Glu Pro Glu Ala Gln
            515                 520                 525

Asn Thr Thr Tyr Leu Trp Trp Val Asn Gly Gln Ser Leu Pro Val Ser
530                 535                 540

Pro Arg Leu Gln Leu Ser Asn Gly Asn Arg Thr Leu Thr Leu Phe Asn
545                 550                 555                 560

Val Thr Arg Asn Asp Ala Arg Ala Tyr Val Cys Gly Ile Gln Asn Ser
                565                 570                 575

Val Ser Ala Asn Arg Ser Asp Pro Val Thr Leu Asp Val Leu Tyr Gly
            580                 585                 590

Pro Asp Thr Pro Ile Ile Ser Pro Pro Asp Ser Ser Tyr Leu Ser Gly
            595                 600                 605

Ala Asn Leu Asn Leu Ser Cys His Ser Ala Ser Asn Pro Ser Pro Gln
        610                 615                 620

Tyr Ser Trp Arg Ile Asn Gly Ile Pro Gln Gln His Thr Gln Val Leu
625                 630                 635                 640
```

```
Phe Ile Ala Lys Ile Thr Pro Asn Asn Asn Gly Thr Tyr Ala Cys Phe
                645                 650                 655

Val Ser Asn Leu Ala Thr Gly Arg Asn Asn Ser Ile Val Lys Ser Ile
                660                 665                 670

Thr Val Ser Ala Ser Gly Thr Ser Pro Gly Leu Ser Ala Gly Ala Thr
                675                 680                 685

Val Gly Ile Met Ile Gly Val Leu Val Gly Val Ala Leu Ile
                690                 695                 700

<210> SEQ ID NO 6
<211> LENGTH: 561
<212> TYPE: PRT
<213> ORGANISM: Cytomegalovirus

<400> SEQUENCE: 6

Met Glu Ser Arg Gly Arg Arg Cys Pro Glu Met Ile Ser Val Leu Gly
1               5                   10                  15

Pro Ile Ser Gly His Val Leu Lys Ala Val Phe Ser Arg Gly Asp Thr
                20                  25                  30

Pro Val Leu Pro His Glu Thr Arg Leu Leu Gln Thr Gly Ile His Val
                35                  40                  45

Arg Val Ser Gln Pro Ser Leu Ile Leu Val Ser Gln Tyr Thr Pro Asp
            50                  55                  60

Ser Thr Pro Cys His Arg Gly Asp Asn Gln Leu Gln Val Gln His Thr
65                  70                  75                  80

Tyr Phe Thr Gly Ser Glu Val Glu Asn Val Ser Val Asn Val His Asn
                85                  90                  95

Pro Thr Gly Arg Ser Ile Cys Pro Ser Gln Glu Pro Met Ser Ile Tyr
                100                 105                 110

Val Tyr Ala Leu Pro Leu Lys Met Leu Asn Ile Pro Ser Ile Asn Val
            115                 120                 125

His His Tyr Pro Ser Ala Ala Glu Arg Lys His Arg His Leu Pro Val
        130                 135                 140

Ala Asp Ala Val Ile His Ala Ser Gly Lys Gln Met Trp Gln Ala Arg
145                 150                 155                 160

Leu Thr Val Ser Gly Leu Ala Trp Thr Arg Gln Gln Asn Gln Trp Lys
                165                 170                 175

Glu Pro Asp Val Tyr Tyr Thr Ser Ala Phe Val Phe Pro Thr Lys Asp
                180                 185                 190

Val Ala Leu Arg His Val Val Cys Ala His Glu Leu Val Cys Ser Met
            195                 200                 205

Glu Asn Thr Arg Ala Thr Lys Met Gln Val Ile Gly Asp Gln Tyr Val
        210                 215                 220

Lys Val Tyr Leu Glu Ser Phe Cys Glu Asp Val Pro Ser Gly Lys Leu
225                 230                 235                 240

Phe Met His Val Thr Leu Gly Ser Asp Val Glu Glu Asp Leu Thr Met
                245                 250                 255

Thr Arg Asn Pro Gln Pro Phe Met Arg Pro His Glu Arg Asn Gly Phe
                260                 265                 270

Thr Val Leu Cys Pro Lys Asn Met Ile Ile Lys Pro Gly Lys Ile Ser
            275                 280                 285

His Ile Met Leu Asp Val Ala Phe Thr Ser His Glu His Phe Gly Leu
        290                 295                 300

Leu Cys Pro Lys Ser Ile Pro Gly Leu Ser Ile Ser Gly Asn Leu Leu
```

-continued

```
                305                 310                 315                 320
Met Asn Gly Gln Gln Ile Phe Leu Glu Val Gln Ala Ile Arg Glu Thr
                    325                 330                 335

Val Glu Leu Arg Gln Tyr Asp Pro Val Ala Leu Phe Phe Phe Asp
                340                 345                 350

Ile Asp Leu Leu Leu Gln Arg Gly Pro Gln Tyr Ser Glu His Pro Thr
                    355                 360                 365

Phe Thr Ser Gln Tyr Arg Ile Gln Gly Lys Leu Glu Tyr Arg His Thr
370                 375                 380

Trp Asp Arg His Asp Glu Gly Ala Ala Gln Gly Asp Asp Val Trp
385                 390                 395                 400

Thr Ser Gly Ser Asp Ser Asp Glu Glu Leu Val Thr Thr Glu Arg Lys
                405                 410                 415

Thr Pro Arg Val Thr Gly Gly Gly Ala Met Ala Gly Ala Ser Thr Ser
                420                 425                 430

Ala Gly Arg Lys Arg Lys Ser Ala Ser Ser Ala Thr Ala Cys Thr Ala
                435                 440                 445

Gly Val Met Thr Arg Gly Arg Leu Lys Ala Glu Ser Thr Val Ala Pro
                450                 455                 460

Glu Glu Asp Thr Asp Glu Asp Ser Asp Asn Glu Ile His Asn Pro Ala
465                 470                 475                 480

Val Phe Thr Trp Pro Pro Trp Gln Ala Gly Ile Leu Ala Arg Asn Leu
                    485                 490                 495

Val Pro Met Val Ala Thr Val Gln Gly Gln Asn Leu Lys Tyr Gln Glu
                500                 505                 510

Phe Phe Trp Asp Ala Asn Asp Ile Tyr Arg Ile Phe Ala Glu Leu Glu
                515                 520                 525

Gly Val Trp Gln Pro Ala Ala Gln Pro Lys Arg Arg Arg His Arg Gln
                530                 535                 540

Asp Ala Leu Pro Gly Pro Cys Ile Ala Ser Thr Pro Lys Lys His Arg
545                 550                 555                 560

Gly

<210> SEQ ID NO 7
<211> LENGTH: 561
<212> TYPE: PRT
<213> ORGANISM: artificial sequence
<220> FEATURE:
<223> OTHER INFORMATION: mutated CMV pp65

<400> SEQUENCE: 7

Met Glu Ser Arg Gly Arg Arg Cys Pro Glu Met Ile Ser Val Leu Gly
1               5                   10                  15

Pro Ile Ser Gly His Val Leu Lys Ala Val Phe Ser Arg Gly Asp Thr
                20                  25                  30

Pro Val Leu Pro His Glu Thr Arg Leu Leu Gln Thr Gly Ile His Val
                35                  40                  45

Arg Val Ser Gln Pro Ser Leu Ile Leu Val Ser Gln Tyr Thr Pro Asp
                50                  55                  60

Ser Thr Pro Cys His Arg Gly Asp Asn Gln Leu Gln Val Gln His Thr
65                  70                  75                  80

Tyr Phe Thr Gly Ser Glu Val Glu Asn Val Ser Val Asn Val His Asn
                    85                  90                  95

Pro Thr Gly Arg Ser Ile Cys Pro Ser Gln Glu Pro Met Ser Ile Tyr
                100                 105                 110
```

```
Val Tyr Ala Leu Pro Leu Lys Met Leu Asn Ile Pro Ser Ile Asn Val
        115                 120                 125

His His Tyr Pro Ser Ala Ala Glu Arg Lys His Arg His Leu Pro Val
    130                 135                 140

Ala Asp Ala Val Ile His Ala Ser Gly Lys Gln Met Trp Gln Ala Arg
145                 150                 155                 160

Leu Thr Val Ser Gly Leu Ala Trp Thr Arg Gln Gln Asn Gln Trp Lys
                165                 170                 175

Glu Pro Asp Val Tyr Tyr Thr Ser Ala Phe Val Phe Pro Thr Lys Asp
                180                 185                 190

Val Ala Leu Arg His Val Val Cys Ala His Glu Leu Val Cys Ser Met
                195                 200                 205

Glu Asn Thr Arg Ala Thr Lys Met Gln Val Ile Gly Asp Gln Tyr Val
    210                 215                 220

Lys Val Tyr Leu Glu Ser Phe Cys Glu Asp Val Pro Ser Gly Lys Leu
225                 230                 235                 240

Phe Met His Val Thr Leu Gly Ser Asp Val Glu Asp Leu Thr Met
                245                 250                 255

Thr Arg Asn Pro Gln Pro Phe Met Arg Pro His Glu Arg Asn Gly Phe
            260                 265                 270

Thr Val Leu Cys Pro Lys Asn Met Ile Ile Lys Pro Gly Lys Ile Ser
            275                 280                 285

His Ile Met Leu Asp Val Ala Phe Thr Ser His Glu His Phe Gly Leu
    290                 295                 300

Leu Cys Pro Lys Ser Ile Pro Gly Leu Ser Ile Ser Gly Asn Leu Leu
305                 310                 315                 320

Met Asn Gly Gln Gln Ile Phe Leu Glu Val Gln Ala Ile Arg Glu Thr
                325                 330                 335

Val Glu Leu Arg Gln Tyr Asp Pro Val Ala Ala Leu Phe Phe Phe Asp
                340                 345                 350

Ile Asp Leu Leu Leu Gln Arg Gly Pro Gln Tyr Ser Glu His Pro Thr
            355                 360                 365

Phe Thr Ser Gln Tyr Arg Ile Gln Gly Lys Leu Glu Tyr Arg His Thr
            370                 375                 380

Trp Asp Arg His Asp Glu Gly Ala Ala Gln Gly Asp Asp Val Trp
385                 390                 395                 400

Thr Ser Gly Ser Asp Ser Asp Glu Glu Leu Val Thr Thr Glu Arg Lys
                405                 410                 415

Thr Pro Arg Val Thr Gly Gly Gly Ala Met Ala Gly Ala Ser Thr Ser
                420                 425                 430

Ala Gly Arg Asn Arg Lys Ser Ala Ser Ser Ala Thr Ala Cys Thr Ala
            435                 440                 445

Gly Val Met Thr Arg Gly Arg Leu Lys Ala Glu Ser Thr Val Ala Pro
    450                 455                 460

Glu Glu Asp Thr Asp Glu Asp Ser Asp Asn Glu Ile His Asn Pro Ala
465                 470                 475                 480

Val Phe Thr Trp Pro Pro Trp Gln Ala Gly Ile Leu Ala Arg Asn Leu
                485                 490                 495

Val Pro Met Val Ala Thr Val Gln Gly Gln Asn Leu Lys Tyr Gln Glu
            500                 505                 510

Phe Phe Trp Asp Ala Asn Asp Ile Tyr Arg Ile Phe Ala Glu Leu Glu
            515                 520                 525
```

-continued

```
Gly Val Trp Gln Pro Ala Ala Gln Pro Lys Arg Arg Arg His Arg Gln
        530                 535                 540
Asp Ala Leu Pro Gly Pro Cys Ile Ala Ser Thr Pro Lys Lys His Arg
545                 550                 555                 560
Gly

<210> SEQ ID NO 8
<211> LENGTH: 536
<212> TYPE: PRT
<213> ORGANISM: artificial sequence
<220> FEATURE:
<223> OTHER INFORMATION: mutated CMV pp65

<400> SEQUENCE: 8

Met Glu Ser Arg Gly Arg Arg Cys Pro Glu Met Ile Ser Val Leu Gly
1               5                   10                  15
Pro Ile Ser Gly His Val Leu Lys Ala Val Phe Ser Arg Gly Asp Thr
                20                  25                  30
Pro Val Leu Pro His Glu Thr Arg Leu Leu Gln Thr Gly Ile His Val
            35                  40                  45
Arg Val Ser Gln Pro Ser Leu Ile Leu Val Ser Gln Tyr Thr Pro Asp
        50                  55                  60
Ser Thr Pro Cys His Arg Gly Asp Asn Gln Leu Gln Val Gln His Thr
65                  70                  75                  80
Tyr Phe Thr Gly Ser Glu Val Glu Asn Val Ser Val Asn Val His Asn
                85                  90                  95
Pro Thr Gly Arg Ser Ile Cys Pro Ser Gln Glu Pro Met Ser Ile Tyr
            100                 105                 110
Val Tyr Ala Leu Pro Leu Lys Met Leu Asn Ile Pro Ser Ile Asn Val
        115                 120                 125
His His Tyr Pro Ser Ala Ala Glu Arg Lys His Arg His Leu Pro Val
130                 135                 140
Ala Asp Ala Val Ile His Ala Ser Gly Lys Gln Met Trp Gln Ala Arg
145                 150                 155                 160
Leu Thr Val Ser Gly Leu Ala Trp Thr Arg Gln Gln Asn Gln Trp Lys
                165                 170                 175
Glu Pro Asp Val Tyr Tyr Thr Ser Ala Phe Val Phe Pro Thr Lys Asp
            180                 185                 190
Val Ala Leu Arg His Val Val Cys Ala His Glu Leu Val Cys Ser Met
        195                 200                 205
Glu Asn Thr Arg Ala Thr Lys Met Gln Val Ile Gly Asp Gln Tyr Val
210                 215                 220
Lys Val Tyr Leu Glu Ser Phe Cys Glu Asp Val Pro Ser Gly Lys Leu
225                 230                 235                 240
Phe Met His Val Thr Leu Gly Ser Asp Val Glu Glu Asp Leu Thr Met
                245                 250                 255
Thr Arg Asn Pro Gln Pro Phe Met Arg Pro His Glu Arg Asn Gly Phe
            260                 265                 270
Thr Val Leu Cys Pro Lys Asn Met Ile Ile Lys Pro Gly Lys Ile Ser
        275                 280                 285
His Ile Met Leu Asp Val Ala Phe Thr Ser His Glu His Phe Gly Leu
290                 295                 300
Leu Cys Pro Lys Ser Ile Pro Gly Leu Ser Ile Ser Gly Asn Leu Leu
305                 310                 315                 320
Met Asn Gly Gln Gln Ile Phe Leu Glu Val Gln Ala Ile Arg Glu Thr
```

-continued

```
                325                 330                 335
Val Glu Leu Arg Gln Tyr Asp Pro Val Ala Ala Leu Phe Phe Phe Asp
            340                 345                 350

Ile Asp Leu Leu Leu Gln Arg Gly Pro Gln Tyr Ser Glu His Pro Thr
        355                 360                 365

Phe Thr Ser Gln Tyr Arg Ile Gln Gly Lys Leu Glu Tyr Arg His Thr
        370                 375                 380

Trp Asp Arg His Asp Glu Gly Ala Ala Gln Gly Asp Asp Val Trp
385                 390                 395                 400

Thr Ser Gly Ser Asp Ser Asp Glu Glu Leu Val Thr Thr Glu Arg Lys
            405                 410                 415

Thr Pro Arg Val Thr Gly Gly Gly Ala Met Ala Gly Ala Ser Thr Ser
            420                 425                 430

Ala Gly Arg Asn Arg Lys Ser Ala Ser Ser Ala Thr Ala Cys Thr Ala
            435                 440                 445

Gly Val Met Thr Arg Gly Arg Leu Lys Ala Glu Ser Thr Val Ala Pro
        450                 455                 460

Glu Glu Asp Thr Asp Glu Asp Ser Asp Asn Glu Ile His Asn Pro Ala
465                 470                 475                 480

Val Phe Thr Trp Pro Pro Trp Gln Ala Gly Ile Leu Ala Arg Asn Leu
            485                 490                 495

Val Pro Met Val Ala Thr Val Gln Gly Gln Asn Leu Lys Tyr Gln Glu
            500                 505                 510

Phe Phe Trp Asp Ala Asn Asp Ile Tyr Arg Ile Phe Ala Glu Leu Glu
        515                 520                 525

Gly Val Trp Gln Pro Ala Ala Gln
        530                 535
```

VEGFR-2 TARGETING IMMUNOTHERAPY APPROACH

CROSS-REFERENCE TO RELATED APPLICATIONS

This application is a national phase entry pursuant to 35 U.S.C. § 371 of International Application No. PCT/EP2018/053918, filed Feb. 16, 2018, which claims priority from EP 17156718.3, filed 17 Feb. 2017, the entire contents and elements of which are herein incorporated by reference for all purposes.

FIELD OF THE INVENTION

The present invention relates to an attenuated strain of Salmonella comprising at least one copy of a DNA molecule comprising an expression cassette encoding a VEGF receptor protein for use in cancer immunotherapy, wherein the cancer is characterized by VEGF receptor protein expressing cancer cells. The present invention further relates to an attenuated strain of Salmonella comprising at least one copy of a DNA molecule comprising an expression cassette encoding a VEGF receptor protein for use in cancer immunotherapy, wherein the cancer is characterized by VEGF receptor protein expressing cancer cells, and wherein the cancer is selected from the group consisting of glioblastoma, carcinoid cancer, kidney cancer, particularly renal cell carcinoma, thyroid cancer, lung cancer, particularly Non-Small Cell Lung Cancer (NSCLC), breast cancer, ovarian cancer, prostate cancer, gastrointestinal cancer, particularly colorectal cancer, more particularly colon cancer, and skin cancer, particularly melanoma. The present invention further relates to an attenuated strain of Salmonella comprising at least one copy of a DNA molecule comprising an expression cassette encoding a VEGF receptor protein for use in cancer immunotherapy in a patient comprising at least one VEGF receptor protein expressing cancer cell.

BACKGROUND OF THE INVENTION

Angiogenesis is a critical factor contributing to solid tumor growth and metastasis. Vascular endothelial growth factor receptor (VEGFR) 2 (also known as KDR or Flk-1) is a high-affinity receptor for vascular endothelial growth factor (VEGF) and is thought to be the major mediator of angiogenesis in solid tumors, as it is implicated in all critical endothelial functions including proliferation, migration, and vessel formation. The tumor neovasculature is lined with endothelial cells that overexpress VEGFR-2 and are readily accessible via the blood stream. The genetic stability of these cells and their ability to support hundreds of tumor cells per endothelial cell make them a prime target for anti-cancer therapy, be it via antibodies, tyrosine kinase inhibitors, or vaccines (Augustin, Trends Pharmacol Sci 1998, 19:216-222). To date, the VEGF/VEGFR2 signaling pathway has been targeted in a number of anti-angiogenic therapy approaches. Compounds like bevacizumab and others, for example small molecules such as sunitinib and axitinib that specifically target the tumor neovasculature have shown efficacy in a range of tumor indications (Powles et al., Br J Cancer 2011, 104(5):741-5); Rini et al., Lancet 2011, 378:1931-1939).

WO 2014/005683 discloses an attenuated mutant strain of Salmonella comprising a recombinant DNA molecule encoding a VEGF receptor protein for use in cancer immunotherapy, particularly for use in the treatment of pancreatic cancer.

WO 2016/202459 discloses an attenuated strain of Salmonella comprising at least one copy of a DNA molecule comprising an expression cassette encoding a VEGF receptor protein, for use in the treatment of cancer, wherein the treatment further comprises the administration of at least one further anti-cancer agent.

WO 2013/09189 discloses a method for growing attenuated mutant Salmonella typhi strains lacking galactose epimerase activity and harboring a recombinant DNA molecule.

VEGF receptors have long been assumed to be restricted to the vasculature of malignancies, i.e. to the tumor stroma. Recent expression analyses, however, revealed the expression of vascular endothelial growth factor receptors, in particular VEGFR-2, on tumor cells themselves. Tumor-specific VEGF receptor expression was observed on cancer cells of various origins. This indicates that VEGF might have additional effects on tumorigenesis besides promoting neovascularization.

OBJECTS OF THE INVENTION

It is an object of the present invention to provide novel safe and efficient cancer immunotherapy approaches targeting VEGF receptors. Such novel therapy approaches would offer major advantages for improving the treatment options for cancer patients.

SUMMARY OF THE INVENTION

Recent expression analyses revealed the tumor-specific expression of vascular endothelial growth factor receptors, in particular VEGFR-2, on cancer cells of various origins. The biological role of tumor-specific VEGF receptor expression however remains unclear. Available data on the effect of VEGFR-2 expression on glioblastoma are highly controversial. Whereas Kessler et al (Oncotarget, 2015) have reported that expression of VEGFR-2 in glioma cells drives glioma cell proliferation and increases resistance of glioma cells to various chemotherapeutics, Lu et al. (Cancer Cell, 2012) have found that VEGF directly and negatively regulates tumor cell invasion via VEGFR-2.

The present invention is based on the surprising finding that a Salmonella-based DNA vaccine targeting a VEGF receptor is particularly efficient against tumors exhibiting tumor-specific VEGF receptor expression—optionally in addition to VEGF receptor expression in the tumor vasculature—as compared to tumors only exhibiting VEGF receptor expression in the tumor vasculature. Within the context of the present invention, the term "tumor-specific VEGF receptor expression" refers to expression of VEGF receptors on the tumor cells themselves as opposed to the tumor vasculature.

Thus, in a first aspect, the present invention relates to an attenuated strain of Salmonella comprising at least one copy of a DNA molecule comprising an expression cassette encoding a VEGF receptor protein for use in cancer immunotherapy, wherein the cancer is characterized by VEGF receptor protein expressing cancer cells.

In a second aspect, the present invention relates to an attenuated strain of Salmonella comprising at least one copy of a DNA molecule comprising an expression cassette encoding a VEGF receptor protein for use in cancer immunotherapy, wherein the cancer is characterized by VEGF receptor protein expressing cancer cells, and wherein the cancer is selected from the group consisting of glioblastoma, carcinoid cancer, kidney cancer, particularly renal cell carcinoma, thyroid cancer, lung cancer, particularly Non-Small Cell Lung Cancer (NSCLC), breast cancer, ovarian cancer, prostate cancer, gastrointestinal cancer, particularly colorectal cancer, more particularly colon cancer, and skin cancer, particularly melanoma.

In a third aspect, the present invention relates to an attenuated strain of *Salmonella* comprising at least one copy of a DNA molecule comprising an expression cassette encoding a VEGF receptor protein for use in cancer immunotherapy in a patient comprising at least one VEGF receptor protein expressing cancer cell.

In particular embodiments, the attenuated strain of *Salmonella* is of the species *Salmonella enterica*. Particularly, the attenuated strain of *Salmonella* is *Salmonella typhi* Ty21a.

In particular embodiments, the expression cassette is a eukaryotic expression cassette. Particularly, the expression cassette comprises a CMV promoter.

In particular embodiments, the VEGF receptor protein is VEGFR-2, particularly human VEGFR-2. Particularly, the VEGF receptor protein is selected from the group consisting of VEGFR-2 having the amino acid sequence as found in SEQ ID NO 1 and a protein that shares at least 80% sequence identity therewith. Particularly, the VEGF receptor protein has the amino acid sequence as found in SEQ ID NO 1.

In particular embodiments, the DNA molecule comprises the kanamycin antibiotic resistance gene, the pMB1 ori and a CMV promoter. In particular such embodiments, the DNA molecule comprises the DNA sequence as found in SEQ ID NO 2.

In particular embodiments, cancer immunotherapy is accompanied by chemotherapy, radiotherapy or biological cancer therapy. In particular such embodiments, the attenuated strain of *Salmonella* is administered before, during or after the chemotherapy or the radiotherapy treatment or the biological cancer therapy, or before and during the chemotherapy or the radiotherapy treatment or the biological cancer therapy.

In particular embodiments, the biological cancer therapy comprises administration of at least one further DNA vaccine encoding a tumor antigen and/or a tumor stroma antigen. In particular such embodiments, said at least one further DNA vaccine encoding a tumor antigen and/or a tumor stroma antigen is selected from at least one further attenuated strain of *Salmonella* comprising at least one copy of a further DNA molecule comprising a further expression cassette encoding a tumor antigen and/or a tumor stroma antigen. Particularly, said at least one further attenuated strain of *Salmonella* is *Salmonella typhi* Ty21a comprising a further eukaryotic expression cassette.

In particular embodiments, said tumor antigen encoded by said at least one further DNA vaccine is selected from the group consisting of human Wilms' Tumor Protein (WT1), human Mesothelin (MSLN), CEA and CMV pp65. Particularly, said tumor antigen encoded by said at least one further DNA vaccine is selected from the group consisting of human Wilms' Tumor Protein (WT1) having the amino acid sequence as found in SEQ ID NO 3 and a protein that shares at least about 80% sequence identity therewith, human Mesothelin (MSLN) having the amino acid sequence as found in SEQ ID NO 4 and a protein that shares at least about 80% sequence identity therewith, human CEA having the amino acid sequence as found in SEQ ID NO 5 and a protein that shares at least about 80% sequence identity therewith, CMV pp65 having the amino acid sequence as found in SEQ ID NO 6 and a protein that shares at least about 80% sequence identity therewith, CMV pp65 having the amino acid sequence as found in SEQ ID NO 7 and a protein that shares at least about 80% sequence identity therewith, and CMV pp65 having the amino acid sequence as found in SEQ ID NO 8 and a protein that shares at least about 80% sequence identity therewith. Particularly, human Wilms' Tumor Protein (WT1) has the amino acid sequence as found in SEQ ID NO 3, human Mesothelin (MSLN) has the amino acid sequence as found in SEQ ID NO 4, human CEA has the amino acid sequence as found in SEQ ID NO 5, and CMV pp65 has the amino acid sequence as found in SEQ ID NO 6, SEQ ID NO 7 or SEQ ID NO 8. In particular embodiments, said tumor stroma antigen encoded by said at least one further DNA vaccine is selected from the group consisting of human fibroblast activation protein (FAP).

In particular embodiments, the attenuated strain of *Salmonella* is administered orally.

In particular embodiments, the single dose of the attenuated strain of *Salmonella* comprises from about $10^5$ to about $10^{11}$, particularly from about $10^6$ to about $10^{10}$, more particularly from about $10^6$ to about $10^9$, more particularly from about $10^6$ to about $10^8$, most particularly from about $10^6$ to about $10^7$ colony forming units (CFU).

In particular embodiments, the attenuated strain of *Salmonella* is for use in individualized cancer immunotherapy comprising the step of assessing the expression pattern of and/or the pre-immune response against at least one VEGF receptor protein, particularly of VEGFR-2 in a patient.

DETAILED DESCRIPTION OF THE INVENTION

In a first aspect, the present invention relates to an attenuated strain of *Salmonella* comprising at least one copy of a DNA molecule comprising an expression cassette encoding a VEGF receptor protein, particularly VEGFR-2, for use in cancer immunotherapy, wherein the cancer is characterized by VEGF receptor protein, particularly VEGFR-2, expressing cancer cells.

Within the context of the present invention, the term "cancer which is characterized by VEGF receptor protein expressing cancer cells" refers to cancer indications characterized by the presence of cancer cells that express at least one VEGF receptor protein, particularly VEGFR-2, on mRNA and/or on protein level. In particular embodiments, the expression of at least one VEGF receptor protein, particularly VEGFR-2 on mRNA and/or protein level is increased as compared to non-cancerous cells of the same tissue type. For instance, the expression of at least one VEGF receptor protein, particularly VEGFR-2 may be increased as compared to non-cancerous cells of the same tissue type of the same patient. In other embodiments, the expression of at least one VEGF receptor protein, particularly VEGFR-2 may be increased as compared to the average expression in non-cancerous cells of the same tissue in a representative healthy subject population. Cancer indications that are characterized by VEGF receptor protein expression include, inter alia, glioblastoma, carcinoid cancer, kidney cancer, particularly renal cell carcinoma, pancreatic cancer, thyroid cancer, lung cancer, particularly Non-Small Cell Lung Cancer (NSCLC), breast cancer, ovarian cancer, prostate cancer, gastrointestinal cancer, particularly colorectal cancer, more particularly colon cancer, and skin cancer, particularly melanoma.

Thus, in a second aspect, the present invention relates to an attenuated strain of *Salmonella* comprising at least one copy of a DNA molecule comprising an expression cassette encoding a VEGF receptor protein, particularly VEGFR-2, for use in cancer immunotherapy, wherein the cancer is characterized by VEGF receptor protein expressing cancer cells, particularly by VEGFR-2 expressing cancer cells, wherein the cancer is selected from the group consisting of glioblastoma, carcinoid cancer, kidney cancer, particularly renal cell carcinoma, thyroid cancer, lung cancer, particularly Non-Small Cell Lung Cancer (NSCLC), breast cancer, ovarian cancer, prostate cancer, gastrointestinal cancer, particularly colorectal cancer, more particularly colon cancer, and skin cancer, particularly melanoma.

One particularly promising indication for VEGFR-2 targeting immunotherapy is glioblastoma. Glioblastoma shows extremely high tumor vascularization. Moreover, VEGFR-2 may be targeted on both the tumor vasculature and the tumor cells. About 20% to 50% of glioblastoma patients show tumor-specific VEGFR-2 expression, which is particularly observed at the invasion front. Furthermore, VEGFR-2 expression was observed in glioma-like stem cells. So far, the treatment options for glioblastoma remain unsatisfactory. For example, the monoclonal antibody avastin targeting VEGF only showed benefits in progression free survival, but not in overall survival.

In a third aspect, the present invention relates to an attenuated strain of *Salmonella* comprising at least one copy of a DNA molecule comprising an expression cassette encoding a VEGF receptor protein, particularly VEGFR-2, for use in cancer immunotherapy in a patient comprising at least one VEGF receptor protein expressing cancer cell, particularly at least one VEGFR-2 expressing cancer cell.

In particular embodiments of the present invention, the patient has been determined to have a cancer characterized by VEGF receptor protein expressing cancer cells or to have at least one VEGF receptor protein expressing cancer cell. In a first step, the patient's tumor-specific VEGF receptor protein expression, e.g. the tumor-specific expression of VEGFR-2, may be assessed on mRNA or protein level, preferably in vitro. For that purpose, tumor tissue samples (e.g., a biopsy) may for example either be stained by immunohistochemistry staining or they may undergo in situ hybridization. Methods for the assessment of tumor-specific antigen expression are well known in the art.

According to the invention, the attenuated *Salmonella* strain functions as the bacterial carrier of the recombinant DNA molecule comprising an expression cassette encoding a VEGF receptor protein for the delivery of said recombinant DNA molecule into a target cell. Such a delivery vector comprising a DNA molecule encoding a heterologous antigen, such as a VEGF receptor protein, is termed DNA vaccine. Thus, the terms "DNA vaccine encoding" and "attenuated strain of *Salmonella* comprising at least one copy of a DNA molecule comprising an expression cassette encoding" are used interchangeably herein.

In the context of the present invention, the term "vaccine" refers to an agent which is able to induce an immune response in a subject upon administration. A vaccine can preferably prevent, ameliorate or treat a disease.

The live attenuated *Salmonella* strain according to the present invention stably carries a recombinant DNA molecule encoding a VEGF receptor protein. It can be used as a vehicle for the oral delivery of this recombinant DNA molecule.

Genetic immunization might be advantageous over conventional vaccination. The target DNA can be detected for a considerable period of time thus acting as a depot of the antigen. Sequence motifs in some plasmids, like GpC islands, are immunostimulatory and can function as adjuvants furthered by the immunostimulation due to LPS and other bacterial components.

Live attenuated *Salmonella* vectors produce their own immunomodulatory factors such as lipopolysaccharides (LPS) in situ which may constitute an advantage over other forms of administration such as microencapsulation. Moreover, the mucosal vaccine according to the present invention has an intra-lymphatic mode of action, which proves to be of benefit. After ingestion of the attenuated vaccine according to the present invention, macrophages and other cells in Peyer's patches of the gut are invaded by the modified bacteria. The bacteria are taken up by these phagocytic cells. Due to their attenuating mutations, bacteria of the *S. typhi* Ty21 strain are not able to persist in these phagocytic cells but die at this time point. The recombinant DNA molecules are released and subsequently transferred into the cytosol of the phagocytic immune cells, either via a specific transport system or by endosomal leakage. Finally, the recombinant DNA molecules enter the nucleus, where they are transcribed, leading to massive VEGF receptor protein expression in the cytosol of the phagocytic cells. The infected cells undergo apoptosis, loaded with the VEGF receptor protein antigen, and are taken up and processed by the gut's immune system. The danger signals of the bacterial infection serve as a strong adjuvant in this process, leading to a strong target antigen specific CD8+ T-cell and antibody response at the level of both systemic and mucosal compartments. The immune response peaks around ten days after vaccination. The lack of anti-carrier response allows boosting with the same vaccine over many times.

In the context of the present invention, the term "attenuated" refers to a bacterial strain of reduced virulence compared to the parental bacterial strain, not harboring the attenuating mutation. Attenuated bacterial strains have preferably lost their virulence but retained their ability to induce protective immunity. Attenuation can be accomplished by deletion of various genes, including virulence, regulatory, and metabolic genes. Attenuated bacteria may be found naturally or they may be produced artificially in the laboratory, for example by adaptation to a new medium or cell culture or they may be produced by recombinant DNA technology. Administration of about $10^{11}$ CFU of the attenuated strain of *Salmonella* according to the present invention preferably causes *Salmonellosis* in less than 5%, more preferably less than 1%, most preferably less than 1%0 of subjects.

In the context of the present invention, the term "comprises" or "comprising" means "including, but not limited to". The term is intended to be open-ended, to specify the presence of any stated features, elements, integers, steps or components, but not to preclude the presence or addition of one or more other features, elements, integers, steps, components or groups thereof. The term "comprising" thus includes the more restrictive terms "consisting of" and "essentially consisting of". In one embodiment the term "comprising" as used throughout the application and in particular within the claims may be replaced by the term "consisting of".

The DNA molecule comprising an expression cassette encoding a VEGF receptor protein is suitably a recombinant DNA molecule, i.e. an engineered DNA construct, preferably composed of DNA pieces of different origin. The DNA molecule can be a linear nucleic acid, or preferably, a circular DNA plasmid generated by introducing an open reading frame encoding a VEGF receptor protein into an expression vector plasmid.

In the context of the present invention, the term "expression cassette" refers to a nucleic acid unit comprising at least one open reading frame (ORF) under the control of regulatory sequences controlling its expression. Expression cassettes can preferably mediate transcription of the included open reading frame encoding an antigen, such as a VEGF receptor protein, in a target cell. Expression cassettes typically comprise a promoter, at least one open reading frame and a transcription termination signal.

In particular embodiments, the attenuated strain of Salmonella is of the species Salmonella enterica. Attenuated derivatives of Salmonella enterica are attractive vehicles for the delivery of heterologous antigens to the mammalian immune system, since S. enterica strains can potentially be delivered via mucosal routes of immunization, i.e. orally or nasally, which offers advantages of simplicity and safety compared to parenteral administration. Furthermore, Salmonella strains elicit strong humoral and cellular immune responses at the level of both systemic and mucosal compartments. Batch preparation costs are low and formulations of live bacterial vaccines are highly stable. Attenuation can be accomplished by deletion of various genes, including virulence, regulatory, and metabolic genes.

Several Salmonella typhimurium strains attenuated by aro mutations have been shown to be safe and effective delivery vehicles for heterologous antigens in animal models.

In particular embodiments, the attenuated strain of Salmonella and the at least one further attenuated strain of Salmonella are Salmonella typhi Ty21a. The live, attenuated S. typhi Ty21a strain is the active component of Typhoral L®, also known as Vivotif® (manufactured by Berna Biotech Ltd., a Crucell Company, Switzerland). It is currently the only licensed live oral vaccine against typhoid fever. This vaccine has been extensively tested and has proved to be safe regarding patient toxicity as well as transmission to third parties (Wandan et al., J. Infectious Diseases 1982, 145:292-295). The vaccine is licensed in more than 40 countries and has been used in millions of individuals including thousands of children for prophylactic vaccination against typhoid fever. It has an unparalleled safety track record. There is no data available indicating that S. typhi Ty21a is able to enter the bloodstream systemically. The live attenuated Salmonella typhi Ty21a vaccine strain thus allows specific targeting of the immune system in the gut, while being safe and well-tolerated. The Marketing Authorization number of Typhoral L® is PL 15747/0001 dated 16 Dec. 1996. One dose of vaccine contains at least $2 \times 10^9$ viable S. typhi Ty21a colony forming units and at least $5 \times 10^9$ non-viable S. typhi Ty21a cells.

This well-tolerated, live oral vaccine against typhoid fever was derived by chemical mutagenesis of the wild-type virulent bacterial isolate S. typhi Ty2 and harbors a loss-of-function mutation in the galE gene resulting in its inability to metabolize galactose. The attenuated bacterial strain is also not able to reduce sulfate to sulfide which differentiates it from the wild-type Salmonella typhi Ty2 strain. With regard to its serological characteristics, the Salmonella typhi Ty21a strain contains the O9-antigen which is a polysaccharide of the outer membrane of the bacteria and lacks the O5-antigen which is in turn a characteristic component of Salmonella typhimurium. This serological characteristic supports the rationale for including the respective test in a panel of identity tests for batch release.

In particular embodiments, the expression cassette is a eukaryotic expression cassette. Particularly, the expression cassette comprises a CMV promoter. In the context of the present invention, the term "eukaryotic expression cassette" refers to an expression cassette which allows for expression of the open reading frame in a eukaryotic cell. It has been shown that the amount of heterologous antigen required to induce an adequate immune response may be toxic for the bacterium and may result in cell death, over-attenuation or loss of expression of the heterologous antigen. Using a eukaryotic expression cassette that is not expressed in the bacterial vector but only in the target cell may overcome this toxicity problem and the protein expressed typically exhibits a eukaryotic glycosylation pattern.

A eukaryotic expression cassette comprises regulatory sequences that are able to control the expression of an open reading frame in a eukaryotic cell, preferably a promoter and a polyadenylation signal. Promoters and polyadenylation signals included in the recombinant DNA molecules comprised by the attenuated strain of Salmonella of the present invention are preferably selected to be functional within the cells of the subject to be immunized. Examples of suitable promoters, especially for the production of a DNA vaccine for humans, include but are not limited to promoters from Cytomegalovirus (CMV), such as the strong CMV immediate early promoter, Simian Virus 40 (SV40), Mouse Mammary Tumor Virus (MMTV), Human Immunodeficiency Virus (HIV), such as the HIV Long Terminal Repeat (LTR) promoter, Moloney virus, Epstein Barr Virus (EBV), and from Rous Sarcoma Virus (RSV), the synthetic CAG promoter composed of the CMV early enhancer element, the promoter, the first exon and the first intron of chicken beta-actin gene and the splice acceptor of the rabbit beta globin gene, as well as promoters from human genes such as human actin, human myosin, human hemoglobin, human muscle creatine, and human metallothionein. In a particular embodiment, the eukaryotic expression cassette contains the CMV promoter. In the context of the present invention, the term "CMV promoter" refers to the strong immediate-early cytomegalovirus promoter.

Examples of suitable polyadenylation signals, especially for the production of a DNA vaccine for humans, include but are not limited to the bovine growth hormone (BGH) polyadenylation site, SV40 polyadenylation signals and LTR polyadenylation signals. In a particular embodiment, the eukaryotic expression cassette included in the recombinant DNA molecule comprised by the attenuated strain of Salmonella of the present invention comprises the BGH polyadenylation site.

In addition to the regulatory elements required for expression of VEGF receptor proteins, like a promoter and a polyadenylation signal, other elements can also be included in the recombinant DNA molecule. Such additional elements include enhancers. The enhancer can be, for example, the enhancer of human actin, human myosin, human hemoglobin, human muscle creatine and viral enhancers such as those from CMV, RSV and EBV.

Regulatory sequences and codons are generally species dependent, so in order to maximize protein production, the regulatory sequences and codons are preferably selected to be effective in the species to be immunized. The person skilled in the art can produce recombinant DNA molecules that are functional in a given subject species.

In particular embodiments, the VEGF receptor protein is VEGFR-2, particularly human VEGFR-2. Particularly, the VEGF receptor protein is selected from the group consisting of VEGFR-2 having the amino acid sequence as found in SEQ ID NO 1 and a protein that shares at least 80% sequence identity therewith. Particularly, the VEGF receptor protein has the amino acid sequence as found in SEQ ID NO 1.

In this context, the term "about" or "approximately" means within 80% to 120%, alternatively within 90% to 110%, including within 95% to 105% of a given value or range.

In the context of the present invention, the term "protein that shares at least about 80% sequence identity with a given protein, e.g., VEGFR-2 having the amino acid sequence as found in SEQ ID NO 1" refers to a protein that may differ in the amino acid sequence encoding the amino acid sequence of said reference protein, e.g., VEGFR-2 having the amino acid sequence of SEQ ID NO 1. The protein may be of natural origin, e.g. a mutant version of a wild-type protein, e.g. a mutant version of a wild type VEGFR-2, or a homolog of a different species, or an engineered protein, e.g., engineered VEGFR-2. It is known that the usage of codons is different between species. Thus, when expressing a heterologous protein in a target cell, it may be necessary, or at least helpful, to adapt the nucleic acid sequence to the codon usage of the target cell. Methods for designing and constructing derivatives of a given protein are well known to anyone of ordinary skill in the art.

The protein that shares at least about 80% sequence identity with a given protein, e.g., VEGFR-2 having the amino acid sequence as found in SEQ ID NO 1, may contain one or more mutations comprising an addition, a deletion and/or a substitution of one or more amino acids in comparison to the reference protein, e.g., VEGFR-2 having the amino acid sequence of SEQ ID NO 1. According to the teaching of the present invention, said deleted, added and/or substituted amino acids may be consecutive amino acids or may be interspersed over the length of the amino acid sequence of the protein that shares at least about 80% sequence identity with a reference protein, e.g., VEGFR-2 having the amino acid sequence as found in SEQ ID NO 1. According to the teaching of the present invention, any number of amino acids may be added, deleted, and/or substitutes, as long as the amino acid sequence identity with the reference protein is at least 80% and the mutated protein is immunogenic. Preferably, the immunogenicity of the protein which shares at least about 80% sequence identity with a given reference protein, e.g., VEGFR-2 having the amino acid sequence as found in SEQ ID NO 1, is reduced by less than 50%, less than 40%, less than 30%, less than 20%, less than 10%, less than 5% or less than 1% compared to said reference protein, e.g., VEGFR-2 having the amino acid sequence as found in SEQ ID NO 1, as measured by ELISA. Methods for designing and constructing protein homologues and for testing such homologues for their immunogenic potential are well known to anyone of ordinary skill in the art. In particular embodiments, the amino acid sequence identity with the reference protein, e.g., VEGFR-2 having the amino acid sequence of SEQ ID NO 1 is at least about 80%, at least about 85%, at least about 90%, or most particularly at least about 95%. Methods and algorithms for determining sequence identity including the comparison of a parental protein and its derivative having deletions, additions and/or substitutions relative to a parental sequence, are well known to the practitioner of ordinary skill in the art. On the DNA level, the nucleic acid sequences encoding the protein that shares at least about 80% sequence identity with a given reference protein, e.g., VEGFR-2 having the amino acid sequence as found in SEQ ID NO 1, may differ to a larger extent due to the degeneracy of the genetic code.

In particular embodiments, the DNA molecule comprises the kanamycin antibiotic resistance gene, the pMB1 ori and a CMV promoter. In particular embodiments, the recombinant DNA molecule is derived from commercially available pVAX1™ expression plasmid (Invitrogen, San Diego, Calif.). This expression vector was modified by replacing the high copy pUC origin of replication by the low copy pMB1 origin of replication of pBR322. The low copy modification was made in order to reduce the metabolic burden and to render the construct more stable. The generated expression vector backbone was designated pVAX10.

In particular embodiments, the DNA molecule comprises the DNA sequence as found in SEQ ID NO 2 (vector backbone pVAX10).

Inserting the ORF encoding human VEGFR-2 having the amino acid sequence of SEQ ID NO 1 into the expression vector backbone via NheI/XhoI yielded the expression plasmid pVAX10.VR2-1 (WO 2013/091898). The expression plasmid pVAX10.VR2-1 is schematically depicted in FIG. 9. The DNA vaccine comprising the attenuated Salmonella strain Ty21a harboring the expression plasmid pVAX10.VR2-1 is designated VXM01 (WO 2013/091898).

In particular embodiments, cancer immunotherapy is accompanied by chemotherapy, radiotherapy or biological cancer therapy. In particular such embodiments, the attenuated strain of Salmonella is administered before, during or after the chemotherapy or the radiotherapy treatment or the biological cancer therapy, or before and during the chemotherapy or the radiotherapy treatment or the biological cancer therapy. For cure of cancer, complete eradication of cancer stem cells may be essential. For maximal efficacy, a combination of different therapy approaches may be beneficial.

In the context of the present invention, the term "biological cancer therapy" refers to cancer therapy involving the use of living organisms including viruses, substances derived from living organisms or laboratory-produced versions of such substances. Some biological therapies for cancer aim at stimulating the body's immune system to act against cancer cells (so called biological cancer immunotherapy). Biological cancer therapy approaches include the delivery of tumor antigens and tumor stroma antigens, e.g. by Salmonella based DNA vaccines, particularly S. typhi Ty21a based DNA vaccines, delivery of therapeutic antibodies as drugs, administration of immunostimulatory cytokines and administration of immune cells, including engineered T cells. Therapeutic antibodies include antibodies targeting tumor antigens or tumor stroma antigens.

In particular embodiments, the biological cancer therapy comprises administration of at least one further DNA vaccine (at least one further attenuated strain of Salmonella comprising at least one copy of a DNA molecule comprising an expression cassette) encoding a tumor antigen and/or a tumor stroma antigen. In particular such embodiments, said at least one further DNA vaccine encoding a tumor antigen and/or a tumor stroma antigen is selected from at least one further attenuated strain of Salmonella comprising at least one copy of a further DNA molecule comprising a further expression cassette encoding a tumor antigen and/or a tumor stroma antigen. Particularly, said at least one further attenuated strain of Salmonella is Salmonella typhi Ty21a comprising a further eukaryotic expression cassette.

In particular embodiments, said tumor antigen encoded by said at least one further DNA vaccine is selected from the group consisting of human Wilms' Tumor Protein (WT1), human Mesothelin (MSLN), human CEA and CMV pp65. Particularly, said tumor antigen encoded by said at least one further DNA vaccine is selected from the group consisting of human Wilms' Tumor Protein (WT1) having the amino acid sequence as found in SEQ ID NO 3 and a protein that shares at least about 80% sequence identity therewith, human Mesothelin (MSLN) having the amino acid sequence as found in SEQ ID NO 4 and a protein that shares at least about 80% sequence identity therewith, human CEA having the amino acid sequence as found in SEQ ID NO 5 and a protein that shares at least about 80% sequence identity therewith, CMV pp65 having the amino acid sequence as found in SEQ ID NO 6 and a protein that shares at least about 80% sequence identity therewith, CMV pp65 having the amino acid sequence as found in SEQ ID NO 7 and a protein that shares at least about 80% sequence identity therewith, and CMV pp65 having the amino acid sequence as found in SEQ ID NO 8 and a protein that shares at least about 80% sequence identity therewith. Particularly, human Wilms' Tumor Protein (WT1) has the amino acid sequence as found in SEQ ID NO 3, human Mesothelin (MSLN) has the amino acid sequence as found in SEQ ID NO 4, human CEA has the amino acid sequence as found in SEQ ID NO 5, and CMV pp65 has the amino acid sequence as found in SEQ ID NO 6, SEQ ID NO 7 or SEQ ID NO 8. In particular embodiments, said tumor stroma antigen encoded by said at least one further DNA vaccine is selected from the group consisting of human fibroblast activation protein (FAP).

In particular embodiments, the attenuated strain of *Salmonella* encoding a VEGF receptor protein is administered prior to or simultaneously with the at least one further DNA vaccine encoding a tumor antigen and/or a tumor stroma antigen.

In the context of the present invention, the term "simultaneously with" means administration of the attenuated strain of *Salmonella* encoding a VEGF receptor protein and the at least one further DNA vaccine encoding a tumor antigen and/or a tumor stroma antigen on the same day, more particularly within 12 hours, more particularly within 2 hours.

In particular embodiments, administration of the attenuated *Salmonella* strain encoding a VEGF receptor protein and the at least further DNA vaccine encoding a tumor antigen and/or a tumor stroma antigen occurs within eight consecutive weeks, more particularly within three to six consecutive weeks. The attenuated *Salmonella* strain encoding a VEGF receptor protein and the at least one further DNA vaccine encoding a tumor antigen or a tumor stroma antigen may be administered via the same route or via different routes. For example, in particular if the at least one further DNA vaccine is a further attenuated strain of *Salmonella*, it may be administered orally.

The single dose of the further attenuated strain of *Salmonella* may comprise from about $10^5$ to about $10^{11}$, particularly from about $10^6$ to about $10^{10}$, more particularly from about $10^6$ to about $10^9$, more particularly from about $10^6$ to about $10^8$, most particularly from about $10^6$ to about $10^7$ colony forming units (CFU).

Chemotherapeutic agents that may be used in combination with the attenuated mutant strain of *Salmonella* of the present invention may be, for example gemcitabine, amifostine (ethyol), cabazitaxel, carboplatin, oxaliplatin, cisplatin, capecitabine, dacarbazine (DTIC), dactinomycin, docetaxel, mechlorethamine, streptozocin, cyclophosphamide, nimustine (ACNU), carmustine (BCNU), lomustine (CCNU), doxorubicin (adriamycin), doxorubicin lipo (doxil), folinic acid, gemcitabine (gemzar), daunorubicin, daunorubicin lipo (daunoxome), epirubicin, procarbazine, ketokonazole, mitomycin, cytarabine, etoposide, methotrexate, 5-fluorouracil (5-FU), vinblastine, vincristine, bleomycin, paclitaxel (taxol), docetaxel (taxotere), permetrexed, aldesleukin, asparaginase, busulfan, carboplatin, cladribine, camptothecin, CPT-11, 10-hydroxy-7-ethyl-camptothecin (SN38), dacarbazine, floxuridine, fludarabine, hydroxyurea, ifosfamide, idarubicin, mesna, interferon alpha, interferon beta, irinotecan, mitoxantrone, topotecan, leuprolide, megestrol, melphalan, mercaptopurine, oxaliplatin, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil, temozolomide and combinations thereof.

Most preferred chemotherapeutic agents according to the invention are cabazitaxel, carboplatin, oxaliplatin, cisplatin, cyclophosphamide, docetaxel, etoposide, gemcitabine, doxorubicin, lomustine, paclitaxel (taxol), irinotecan, vincristine, vinblastine, vinorelbin, folinic acid, 5-fluorouracil, bleomycin and temozolomide, especially gemcitabine.

In particular embodiments, cancer immunotherapy is accompanied by a combination of chemotherapy and radiotherapy. In particular such embodiments, chemotherapy comprises administration of temozolomide.

In particular embodiments, the attenuated strain of *Salmonella* is administered orally. Oral administration is simpler, safer and more comfortable than parenteral administration. However, it has to be noted that the attenuated strain of *Salmonella* encoding a VEGF receptor protein may also be administered by any other suitable route. Preferably, a therapeutically effective dose is administered to the subject, and this dose depends on the particular application, the type of malignancy, the subject's weight, age, sex and state of health, the manner of administration and the formulation, etc. administration may be single or multiple, as required.

The attenuated strain of *Salmonella* encoding a VEGF receptor protein may be provided in the form of a solution, a suspension, a lyophilisate, an enteric coated capsule, or any other suitable form. Typically, the attenuated strain of *Salmonella* is formulated as drinking solution. This embodiment offers the advantage of improved patient compliance. Preferably, the drinking solution comprises means to neutralize gastric acids at least to a certain degree, i.e. to bring the pH of the gastric juice closer to a pH of 7. Preferably, the drinking solution is a buffered suspension comprising the attenuated strain of *Salmonella* encoding a VEGF receptor protein. In a particular embodiment, the buffered suspension is obtained by suspending the attenuated strain of *Salmonella* in a suitable buffer, preferably containing 2.6 g sodium hydrogen carbonate, 1.7 g L-ascorbic acid, 0.2 g lactose monohydrate and 100 ml of drinking water.

The attenuated strain of *Salmonella* encoding a VEGF receptor protein is surprisingly effective at relatively low doses. The efficacy of the attenuated strain of *Salmonella* encoding a VEGF receptor protein is particularly high in cancers with cancer-specific VEGF receptor protein expression. Administration of low doses of live bacterial vaccines minimizes the risk of excretion and thus of transmission to third parties.

In particular embodiments, the single dose of the attenuated strain of *Salmonella* encoding a VEGF receptor protein, particularly *Salmonella typhi* Ty21a encoding human VEGFR-2, comprises from about $10^5$ to about $10^{11}$, particularly from about $10^6$ to about $10^{10}$, more particularly from about $10^6$ to about $10^9$, more particularly from about $10^6$ to about $10^8$, most particularly from about $10^6$ to about $10^7$ colony forming units (CFU).

In this context, the term "about" or "approximately" means within a factor of 3, alternatively within a factor of 2, including within a factor of 1.5 of a given value or range.

In particular embodiments, the attenuated strain of *Salmonella* is for use in individualized cancer immunotherapy comprising the step of assessing the expression pattern of and/or the pre-immune response against at least one VEGF receptor protein, particularly of VEGFR-2 in a patient. Alternatively the attenuated strain of *Salmonella* is for use in cancer immunotherapy in a patient wherein the patient has been determined to have a cancer characterized by VEGF receptor protein (e.g., VEGFR-2) expressing cancer cells or to have at least one VEGF receptor protein (e.g., VEGFR-2) expressing cancer cell, particularly by assessing the expression pattern of and/or the pre-immune response against at least one VEGF receptor protein, particularly of VEGFR-2. The patient's VEGF receptor protein expression and/or the patient's pre-immune responses against a VEGF receptor protein may be assessed in a first step for example by companion diagnostics. Methods for assessing the expression of a target gene, such as VEGFR-2, either on mRNA or on protein level are well known to any one of ordinary skill in the art. For instance, immunohistochemistry staining, flow cytometry methods or RNA sequencing, or alternative methods using labelling can be used to identify the level of target expression in the tumor. Similarly, methods for assessing a patient's pre-immune response against a given protein, such as VEGFR-2, are well known to any one of ordinary skill in the art. A patient's pre-existing VEGFR-2 specific T-cell pool can be detected by e.g. ELISpot or multimer FACS analysis. High tumor-specific VEGFR-2 expression and/or the occurrence of pre-immune responses against VEGFR-2 are prognostic indicators for the predisposition of a patient to respond especially favorably to the treatment with the attenuated strain of *Salmonella* encoding VEGFR-2.

It may be favorable dependent on the occurrence of possible side effects, to include treatment with antibiotics or anti-inflammatory agents.

Should adverse events occur that resemble hypersensitivity reactions mediated by histamine, leukotrienes, or cytokines, treatment options for fever, anaphylaxis, blood pressure instability, bronchospasm, and dyspnoea are available. Treatment options in case of unwanted T-cell derived auto-aggression are derived from standard treatment schemes in acute and chronic graft vs. host disease applied after stem cell transplantation. Cyclosporin and glucocorticoids are proposed as treatment options.

In the unlikely case of systemic *Salmonella typhi* Ty21a type infection, appropriate antibiotic therapy is recommended, for example with fluoroquinolones including ciprofloxacin or ofloxacin. Bacterial infections of the gastrointestinal tract are to be treated with respective agents, such as rifaximin.

The attenuated strain of *Salmonella* encoding a VEGF receptor protein may be provided in a pharmaceutical composition. The pharmaceutical composition may be in the form of a solution, a suspension, an enteric coated capsule, a lyophilized powder or any other form suitable for the intended use.

The pharmaceutical composition may further comprise one or more pharmaceutically acceptable excipients.

In the context of the present invention, the term "excipient" refers to a natural or synthetic substance formulated alongside the active ingredient of a medication. Suitable excipients include antiadherents, binders, coatings, disintegrants, flavors, colors, lubricants, glidants, sorbents, preservatives and sweeteners.

In the context of the present invention, the term "pharmaceutically acceptable" refers to molecular entities and other ingredients of pharmaceutical compositions that are physiologically tolerable and do not typically produce untoward reactions when administered to a mammal (e.g., human). The term "pharmaceutically acceptable" may also mean approved by a regulatory agency of a Federal or a state government or listed in the U.S. Pharmacopeia or other generally recognized pharmacopeia for use in mammals, and, more particularly, in humans.

In particular embodiments, the pharmaceutical composition is provided as drinking solution. This embodiment offers the advantage of improved patient compliance and allows for rapid, feasible and affordable mass vaccination programs.

In particular, suitable drinking solutions comprise means to neutralize gastric acids to at least to a certain degree, i.e. to bring the pH of the gastric juice closer to a pH of 7. In a particular embodiment, the drinking solution is a buffered suspension obtained by suspending the attenuated strain of *Salmonella* according to the present invention in a suitable buffer, preferably in a buffer that neutralizes gastric acids to at least a certain degree, preferably in a buffer containing 2.6 g sodium hydrogen carbonate, 1.7 g L-ascorbic acid, 0.2 g lactose monohydrate and 100 ml of drinking water.

In particular embodiments, cancer immunotherapy comprises a single or multiple administrations of the attenuated strain of *Salmonella* encoding a VEGF receptor protein or a pharmaceutical composition comprising the same. The single dose of the administrations may be the same or different. In particular, cancer immunotherapy comprises 1, 2, 3, 4, 5 or 6 administrations of the attenuated strain of *Salmonella* encoding a VEGF receptor protein, preferably wherein the multiple administrations occur within three to six consecutive months.

SHORT DESCRIPTION OF FIGURES

FIG. 1: Amino acid sequence of human VEGFR-2 (SEQ ID NO 1), which is encoded by VEGFR-2 cDNA contained in plasmid pVAX10.VR2-1

FIG. 2: Nucleic acid sequence comprised in empty expression vector pVAX10 (sequence of expression vector pVAX10 without the portion of the multiple cloning site which is located between the restriction sites NheI and XhoI (SEQ ID NO 2).

FIG. 3: Amino acid sequence of truncated (zinc-finger domain deleted) human WT-1 encoded by WT-1 cDNA contained in plasmid pVAX10.hWT1 (SEQ ID NO 3)

FIG. 4: Amino acid sequence of human MSLN encoded by MSLN cDNA contained in plasmid pVAX10.hMSLN (SEQ ID NO 4)

FIG. 5: Amino acid sequence of human CEA encoded by CEA cDNA contained in plasmid pVAX10.hCEA (SEQ ID NO 5)

FIG. 6: Amino acid sequence of CMV pp65 encoded by CMV pp65 cDNA contained in plasmid pVAX10.CMV pp65_1 (SEQ ID NO 6)

FIG. 7: Amino acid sequence of CMV pp65 encoded by CMV pp65 cDNA contained in plasmid pVAX10.CMV pp65_2 (SEQ ID NO 7)

FIG. 8: Amino acid sequence of CMV pp65 encoded by CMV pp65 cDNA contained in plasmid pVAX10.CMV pp65_3 (SEQ ID NO 8)

FIG. 9: Plasmid map of pVAX10.VR2-1

Figure 10E:
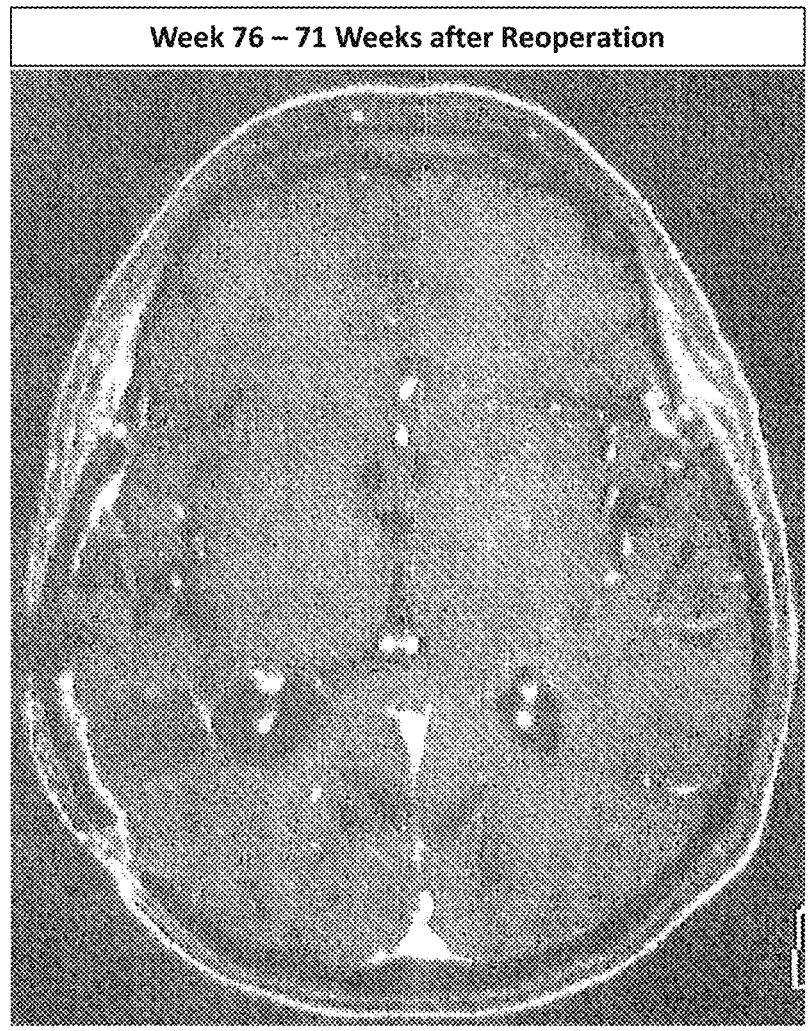

FIGS. 10A-E: Brain MRI images of patient 2605: baseline (FIG. 10A), day 35—before reoperation (FIG. 10B), week 12 after reoperation (FIG. 10C), week 20 after reoperation (FIG. 10D), and week 76 after reoperation (FIG. 10E).

EXAMPLES

Example 1 VXM01 Treatment of Patients with Operable Recurrence of Glioblastoma The aim of this study was to examine safety, tolerability, immune and biomarker response to VEGFR-2 encoding DNA vaccine VXM01.

The study was conducted in patients with operable recurrence of a glioblastoma who have failed at least one standard treatment that must have included radiochemotherapy with temozolomide. All patients received DNA vaccine VXM01 as an add-on to their standard therapy.

The study consisted of a screening period, a treatment and observation period up to month 3, a tumor follow-up from month 3 to month 12 and a boosting treatment period between week 8 and week 48 during the tumor follow-up period. After study end, patients are followed up for up to 2 years.

The treatment and observation period included one oral administration of VXM01 each on day 1, 3, 5 and 7 and reoperation at 5±1 weeks after inclusion. In the boosting treatment period VXM01 was administered in oral 4-weekly single boosting doses at weeks 8, 12, 16, 20, 24, 28, 32, 36, 40, 44 and 48.

VXM01 was administered orally at single doses of $10^6$ and $10^7$ colony forming units (CFU)/ml.

Five out of nine glioblastoma patients showed a favorable course of disease.

Patient 2605:

Patient 2605 is a 55-year-old female patient with recurrent glioblastoma WHO grade IV. Previous cancer treatment included a first operation of glioblastoma and a first line radiochemotherapy with Gy 60 followed by 75 $mg/m^2$ temozolomide.

The patient was treated with VXM01 at a dose of $10^6$ CFU. VXM01 treatment was started with 4 initial administrations on study day 1, 3, 5 and 7 and continued after the routine operation on day 35 with 4-weekly boosting administrations starting on week 8. At week 10, lomustine/etoposide chemotherapy was started on top of VXM01.

The tumor reference target lesion at the screening visit was 25×10 mm. Tumor size development is summarized in Table 1:

TABLE 1

| Target Lesion | Tumor Diameter 1 [mm] | Tumor Diameter 2 [mm] |
|---|---|---|
| Baseline | 25 | 10 |
| Day 10 | 28 | 13 |
| Day 21 | 27 | 13 |
| Day 35 | 25 | 12 |
| Week 12 | 0 | 0 |
| Week 20 | 0 | 0 |
| Week 36 | 0 | 0 |
| Week 52 | 0 | 0 |
| Week 60 | 0 | 0 |
| Week 76 | 0 | 0 |

The respective MRI images at baseline at day 35, week 12, week 20 and week 76 are depicted in FIGS. 10A-E.

The tumor size tended to decrease between study day 10 and the routine operation on day 35 from 28×13 mm to 25×12 mm. According to RANO criteria, this was assessed as stable disease (SD). At week 12, 7 weeks after the routine reoperation on day 35, the assessment according the RANO criteria was progressive disease (PD) due to the occurrence of a new non-target lesion. After the operation, there was no visible "target lesion" on the MRI report week 12. Lomustine/etoposide chemotherapy was started on top of VXM01. At week 20 (i.e. 15 weeks after reoperation), the tumor was assessed as stable disease (SD) according to RANO criteria. At week 36, lomustine/etoposide chemotherapy was stopped and patient was continued to be treated with VXM01 every 4 weeks and treatment has not been stopped until filing of this application.

The Karnofsky Index was 100% on screening and 90% at week 12.

Immunohistochemistry staining of the primary tumor sample collected pre-study revealed that the tumor cells of this patient expressed VEGFR-2. In the recurrent tumor sample on day 35, after treatment with VXM01, the tumor cells were shown not to express VEGFR-2.

In tumor tissue immunohistochemistry CD8+ T-cells increased in the recurrent tumor after VXM01 treatment compared to primary tumor by factor 2.3.

The invention claimed is:

1. A method of treating cancer in a human patient comprising:
   determining that the patient has a cancer comprising VEGFR-2 expressing cancer cells or has at least one cancer cell expressing VEGFR-2, and
   orally administering to the patient having the cancer comprising VEGFR-2 expressing cancer cells or the at least one cancer cell expressing VEGFR-2, a therapeutically effective dose of a live attenuated strain of *Salmonella* comprising at least one copy of a DNA molecule comprising a eukaryotic expression cassette encoding VEGFR-2,
   wherein the live attenuated strain of *Salmonella* is *Salmonella typhi* Ty21a, and wherein the VEGFR-2 comprises the amino acid sequence set forth in SEQ ID NO: 1 or an amino acid sequence that has at least 95% sequence identity to SEQ ID NO: 1.

2. The method of claim 1, wherein the determining comprises assessment of VEGFR-2 mRNA expression in cancer cells from the patient.

3. The method of claim 1, wherein the determining comprises assessment of VEGFR-2 protein expression in cancer cells from the patient.

4. The method of claim 1, wherein the cancer is selected from the group consisting of glioblastoma, carcinoid cancer, kidney cancer, renal cell carcinoma, thyroid cancer, lung cancer, Non-Small Cell Lung Cancer (NSCLC), breast cancer, ovarian cancer, prostate cancer, gastrointestinal cancer, colorectal cancer, colon cancer, skin cancer, and melanoma.

5. The method of claim 1, wherein the DNA molecule comprises the kanamycin antibiotic resistance gene, the pMB1 ori and a CMV promoter.

6. The method of claim 1, further comprising administering chemotherapy, radiotherapy or biological cancer therapy, wherein the attenuated strain of *Salmonella typhi* Ty21a is administered before, during or after the chemotherapy or the radiotherapy treatment or the biological cancer therapy, or before and during the chemotherapy or the radiotherapy treatment or the biological cancer therapy.

7. The method of claim 6, wherein the biological cancer therapy comprises administration of at least one further DNA vaccine encoding a tumor antigen and/or a tumor stroma antigen.

8. The method of claim 7, wherein said tumor antigen encoded by said at least one further DNA vaccine is selected from the group consisting of human Wilms' Tumor Protein (WT1), human Mesothelin (MSLN), human CEA and CMV pp65.

9. The method of claim 8, wherein said tumor antigen is selected from the group consisting of human Wilms' Tumor Protein (WT1) comprising the amino acid sequence as set forth in SEQ ID NO 3, a protein that has at least 80% sequence identity with SEQ ID NO: 3, human Mesothelin (MSLN) comprising the amino acid sequence as set forth in SEQ ID NO 4, a protein that has at least 80% sequence identity with SEQ ID NO: 4, human CEA comprising the amino acid sequence as set forth in SEQ ID NO 5, a protein that has at least 80% sequence identity with SEQ ID NO: 5, CMV pp65 comprising the amino acid sequence as set forth in SEQ ID NO 6, a protein that has at least 80% sequence identity with SEQ ID NO: 6, CMV pp65 comprising the amino acid sequence as set forth in SEQ ID NO 7, a protein that has at least 80% sequence identity with SEQ ID NO: 7, and CMV pp65 comprising the amino acid sequence as set forth in SEQ ID NO 8, and a protein that has at least 80% sequence identity with SEQ ID NO: 8.

10. The method of claim 7, wherein said tumor stroma antigen encoded by said at least one further DNA vaccine is human fibroblast activation protein (FAP).

11. The method of claim 1, wherein a single therapeutically effective dose of the *Salmonella typhi* Ty21a comprises from about $10^5$ to about $10^{11}$ colony forming units (CFU).

12. The method of claim 1, wherein the method comprises assessing the expression pattern of and/or the pre-immune response against the VEGFR-2 in the patient.

13. The method of claim 5, wherein the DNA molecule comprises the sequence of SEQ ID NO: 2.

14. The method of claim 7, wherein the at least one further DNA vaccine encoding the tumor antigen and/or the tumor stroma antigen comprises a live attenuated strain of *Salmonella* comprising at least one copy of a DNA molecule comprising an expression cassette encoding the tumor antigen and/or the tumor stroma antigen.

15. The method of claim 11, wherein the single dose of the *Salmonella typhi* Ty21a comprises from about $10^6$ to about $10^9$ CFU.

16. The method of claim 11, wherein the single dose of the *Salmonella typhi* Ty21a comprises from about $10^6$ to about $10^8$ CFU.

17. The method of claim 1, wherein the cancer is glioblastoma.

18. The method of claim 1, wherein the cancer is colorectal cancer or colon cancer.

19. The method of claim 1, wherein the cancer is kidney cancer or renal cell carcinoma.

20. The method of claim 1, wherein the cancer is lung cancer or Non-Small Cell Lung Cancer (NSCLC).

21. A method of treating cancer in a human patient comprising:
determining that the patient has at least one cancer cell expressing VEGFR-2, and
orally administering to the patient having said cancer cell, a therapeutically effective dose of a live attenuated strain of *Salmonella* comprising at least one copy of a DNA molecule comprising a eukaryotic expression cassette encoding VEGFR-2,
wherein the live attenuated strain of *Salmonella* is *Salmonella typhi* Ty21a, and wherein the VEGFR-2 comprises the amino acid sequence set forth in SEQ ID NO: 1 or an amino acid sequence that has at least 95% sequence identity to SEQ ID NO: 1.

* * * * *

UNITED STATES PATENT AND TRADEMARK OFFICE
CERTIFICATE OF CORRECTION

| | | |
|---|---|---|
| PATENT NO. | : 10,980,868 B2 | Page 1 of 1 |
| APPLICATION NO. | : 16/486425 | |
| DATED | : April 20, 2021 | |
| INVENTOR(S) | : Lubenau | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 71 days.

Signed and Sealed this
Thirtieth Day of August, 2022

Katherine Kelly Vidal
*Director of the United States Patent and Trademark Office*